(12) United States Patent
Frey et al.

(10) Patent No.: US 7,123,029 B2
(45) Date of Patent: Oct. 17, 2006

(54) CIRCUIT ARRANGEMENT, ELECTROCHEMICAL SENSOR, SENSOR ARRANGEMENT, AND METHOD FOR PROCESSING A CURRENT SIGNAL PROVIDED VIA A SENSOR ELECTRODE

(75) Inventors: Alexander Frey, Taufkirchen (DE); Christian Paulus, Weilheim (DE); Meinrad Schienle, Ottobrunn (DE); Roland Thewes, Grobenzell (DE)

(73) Assignee: Siemens AG, Munich (DE)

( * ) Notice: Subject to any disclaimer, the term of this patent is extended or adjusted under 35 U.S.C. 154(b) by 148 days.

(21) Appl. No.: 10/913,706

(22) Filed: Aug. 5, 2004

(65) Prior Publication Data
US 2005/0068046 A1 Mar. 31, 2005

Related U.S. Application Data

(63) Continuation-in-part of application No. PCT/DE03/00123, filed on Jan. 17, 2003.

(30) Foreign Application Priority Data
Feb. 5, 2002 (DE) ................ 102 04 652

(51) Int. Cl.
G01R 27/26 (2006.01)
G01N 27/26 (2006.01)
(52) U.S. Cl. ............... 324/686; 204/401; 204/775
(58) Field of Classification Search ............. 324/686; 204/401; 320/161
See application file for complete search history.

(56) References Cited
U.S. PATENT DOCUMENTS
3,711,779 A 1/1973 Allington
4,199,728 A 4/1980 Carpenter 5,389,215 A * 2/1995 Horiuchi et al. ............ 205/775
6,770,190 B1 * 8/2004 Milanovski et al. ..... 205/777.5
6,787,368 B1 * 9/2004 Wong et al. ................ 436/518
6,922,081 B1 * 7/2005 Frey et al. .................... 326/88
2004/0063152 A1 * 4/2004 Gumbrecht et al. ......... 435/7.1
2004/0072158 A1 * 4/2004 Henkens et al. ............... 435/6

FOREIGN PATENT DOCUMENTS

| DE | 196 10 115 A1 | 9/1997 |
|----|---|---|
| DE | 102 04 652 A1 | 8/2003 |
| EP | 0 634 611 A1 | 1/1995 |
| WO | WO-97/21094 A1 | 6/1997 |
| WO | WO-99/38612 A1 | 8/1999 |

(Continued)

OTHER PUBLICATIONS

Thewes, Roland, et al., "Sensor Arrays for Fully-Electronic DNA Detection on CMOS", Solid State Circuits Conference, Digest of Technical Papers, ISSCC. 2002 IEEE International, vol. 2, Feb. 3-7, 2002.

(Continued)

Primary Examiner—Anjan Deb
Assistant Examiner—John Zhu
(74) Attorney, Agent, or Firm—Dickstein, Shapiro, LLP.

(57) ABSTRACT

Circuit arrangement having a sensor electrode, a first circuit unit, which is electrically coupled to the sensor electrode, and a second circuit unit, which has a first capacitor. The first circuit unit holds an electrical potential of the sensor electrode in a predetermined first reference range around a predetermined electrical desired potential by coupling the first capacitor and the sensor electrode such that there is a matching of their electrical potentials. If the second circuit unit detects the electrical potential of the first capacitor being outside a second reference range, the second circuit unit brings the first capacitor to a first electrical reference potential.

21 Claims, 10 Drawing Sheets

FOREIGN PATENT DOCUMENTS

WO   WO-00/12759 A1   3/2000
WO   WO-02/33397 A1   4/2002

OTHER PUBLICATIONS

Breten, Madalina, et al., "Integrating Data Converters for Picoampere Currents from Electrochemical Transducers", IEEE International Symposium on Circuits and Systems, May 28-31, 2000, vol. 5, pp. 709-712.

Hintsche et al., "Microbiosensors using electrodes made in Si-technology", Frontiers in Biosenorics, 1997.

Van Gerwen, Peter, et al., "Nanoscaled Interdigitated Electrode Arrays for Biochemical Sensors", 1997 International Conference on Solid-State Sensors and Activators, Jun. 18-19, 1997, pp. 907-910.

Paeschke, et al., "Voltrammetric Multichannel Measurements Using Silicon Fabricated Microelectrode Arrays", Electroanalysis, Jul. 27, 1996, vol. 7, No. 1, pp. 1-8.

Franz Hofmann, et al., "Passive DNA Sensor with Gold Electrodes Fabricated in a CMOS Backend Process", Proceedings of the European Solid State Device Research Conference (EDDSERC), Sep. 22, pp. 487-490.

* cited by examiner

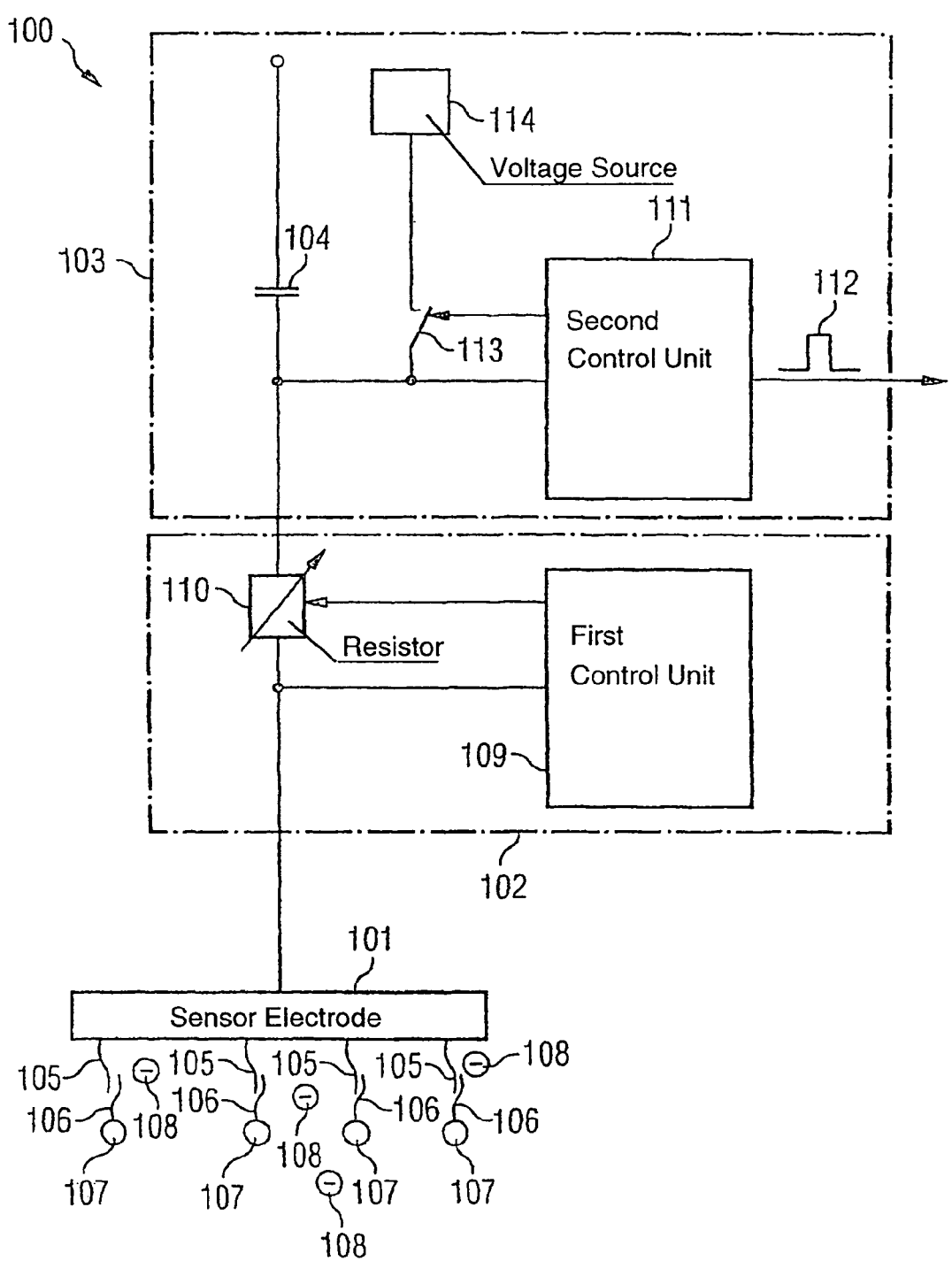

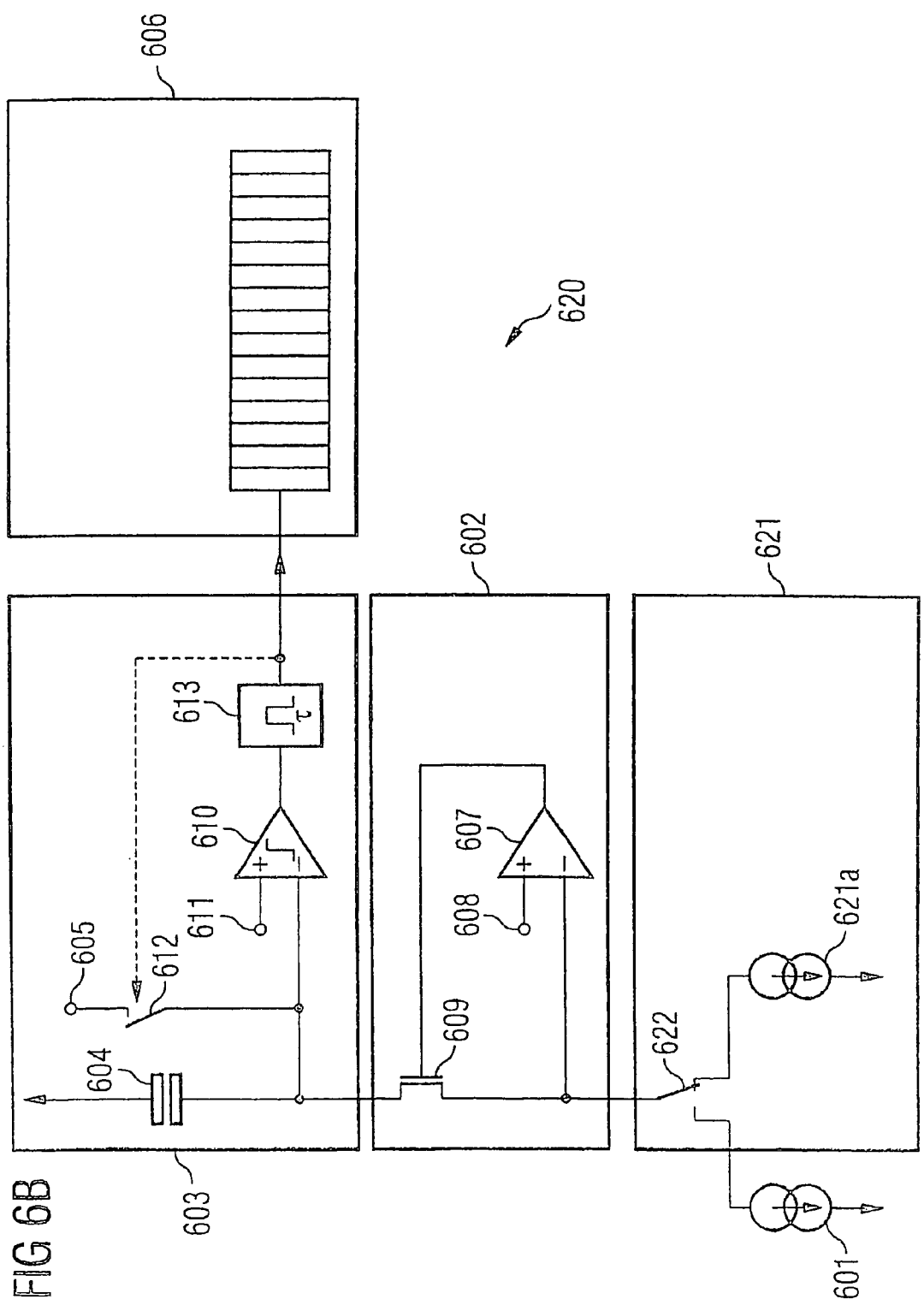

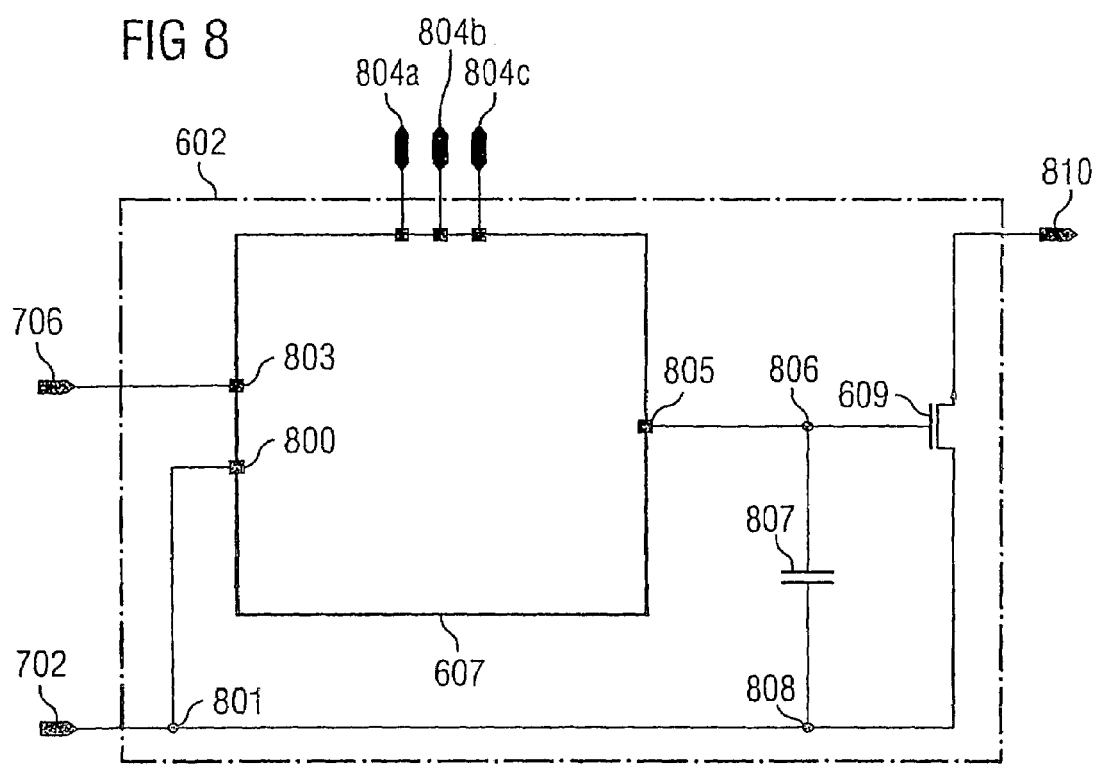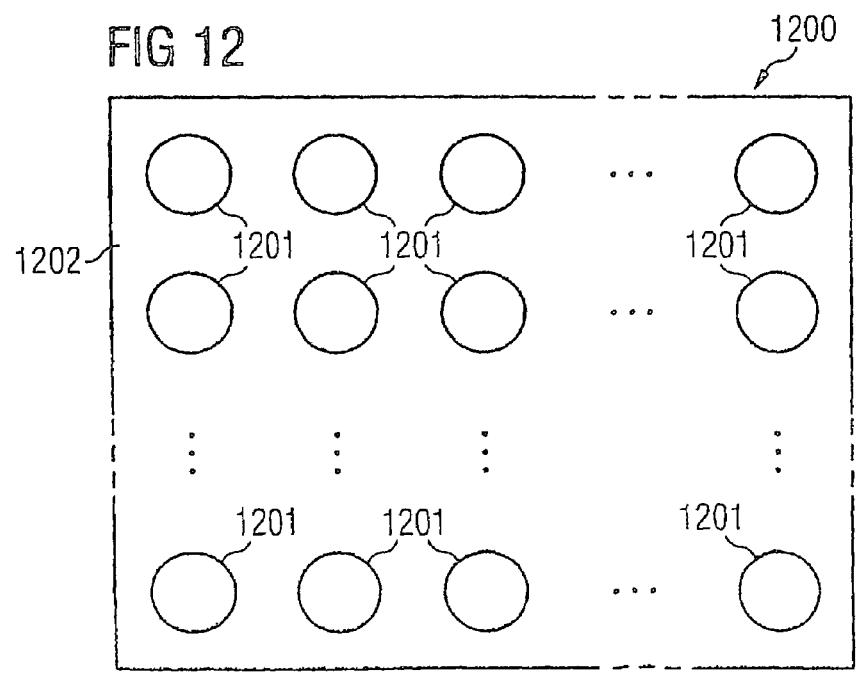

CIRCUIT ARRANGEMENT, ELECTROCHEMICAL SENSOR, SENSOR ARRANGEMENT, AND METHOD FOR PROCESSING A CURRENT SIGNAL PROVIDED VIA A SENSOR ELECTRODE

CROSS-REFERENCE TO RELATED APPLICATION

This application is a continuation of International Patent Application Ser. No. PCT/DE03/00123, filed Jan. 17, 2003, which published in German on Aug. 14, 2003 as WO 03/067238.

FIELD OF THE INVENTION

The invention relates to a circuit arrangement, an electrochemical sensor, a sensor arrangement and a method for processing a current signal provided via a sensor electrode.

BACKGROUND OF THE INVENTION

FIG. 2A and FIG. 2B show a biosensor chip, as described in Hintsche, R., Paeschke, M., Uhlig, A., Seitz, R. (1997) "Microbiosensors using Electrodes made in Si-technology", Frontiers in Biosensorics, Fundamental Aspects, Scheller, F W., Schubert, F., Fedrowitz, J. (eds.), Birkhauser Verlag Basle, Switzerland, pp. 267–283. The sensor 200 has two electrodes 201, 202 made of gold, which are embedded in an insulator layer 203 made of electrically insulating material. Connected to the electrodes 201, 202 are electrode terminals 204, 205, by means of which the electrical potential can be applied to the electrode 201, 202. The electrodes 201, 202 are configured as planar electrodes. DNA probe molecules 206 (also referred to as capture molecules) are immobilized on each electrode 201, 202 (cf. FIG. 2A). The immobilization is effected in accordance with the gold-sulfur coupling. The analyte to be investigated, for example an electrolyte 207 is applied on the electrodes 201, 202.

If the electrolyte 207 contains DNA strands 208 with a base sequence which is complementary to the sequence of the DNA probe molecules 206, i.e. which sterically match the capture molecules in accordance with the key/lock principle, then these DNA strands 208 hybridize with the DNA probe molecules 206 (cf. FIG. 2B).

Hybridization of a DNA probe molecule 206 and a DNA strand 208 takes place only when the sequences of the respective DNA probe molecule and of the corresponding DNA strand 208 are complementary to one another. If this is not the case, then no hybridization takes place. Thus, a DNA probe molecule having a predetermined sequence is in each case only capable of binding a specific DNA strand, namely the one with a respectively complementary sequence, that is to say of hybridizing with it, which results in the high degree of selectivity of the sensor 200.

If hybridization takes place, then the value of the impedance between the electrodes 201 and 202 changes, as can be seen from FIG. 2B. This changed impedance is detected by applying a suitable electrical voltage to the electrode terminals 204, 205 and by registering the current resulting from this.

In the case of hybridization, the impedance between the electrodes 201, 202 changes. This can be attributed to the fact that both the DNA probe molecules 206 and the DNA strands 208, which possibly hybridize with the DNA probe molecules 206, have poorer electrical conductivity than the electrolyte 207 and thus, as can be seen, in part electrically shield the respective electrode 201, 202.

In order to improve the measurement accuracy, it is known from van Gerwen, P. (1997) "Nanoscaled Interdigitated Electrode Arrays for Biochemical Sensors", IEEE, International Conference on Solid-State Sensors and Actuators, Jun. 16–19 1997, Chicago, pp. 907–910, to use a plurality of electrode pairs 201, 202 and to arrange the latter in parallel with one another, these being arranged intermeshed with one another, as can be seen, so that the result is a so-called interdigital electrode 300, FIG. 3A showing the plan view thereof and FIG. 3B showing the cross-sectional view thereof along the section line I–I' from FIG. 3A.

Furthermore, principles relating to a reduction/oxidation recycling process for registering macromolecular biomolecules are known for example from Hintsche et al., and Paeschke, M., Dietrich, F., Uhlig, A., Hintsche, R. (1996) "Voltammetric Multichannel Measurements Using Silicon Fabricated Microelectrode Arrays", Electroanalysis, Vol. 7, No. 1, pp. 1–8. The reduction/oxidation recycling process, also referred to hereinafter as the redox recycling process, will be explained in more detail below with reference to FIG. 4A, FIG. 4B, FIG. 4C.

FIG. 4A shows a biosensor 400 having a first electrode 401 and a second electrode 402, which are applied on an insulator layer 403. A holding region 404 is applied on the first electrode 401 made of gold. The holding region 404 serves for immobilizing the DNA probe molecules 405 on the first electrode 401. Such a holding region is not provided on the second electrode 402.

If DNA strands 407 having a sequence which is complementary to the sequence of the immobilized DNA probe molecules 405 are intended to be registered by means of the biosensor 400, then the sensor 400 is brought into contact with a solution to be investigated, for example an electrolyte 406, in such a way that DNA strands 407 possibly contained in the solution 406 to be investigated can hybridize with the complementary sequence to the sequence of the DNA probe molecules 405.

FIG. 4B shows the case where the DNA strands 407 to be registered are contained in the solution 406 to be investigated and have hybridized with the DNA probe molecules 405.

The DNA strands 407 in the solution to be investigated are marked with an enzyme 408, with which it is possible to cleave molecules described below into partial molecules, at least one of which is redox-active. It is customary to provide a considerably larger number of DNA probe molecules 405 than there are DNA strands 407 to be determined contained in the solution 406 to be investigated.

After the DNA strands 407 possibly contained in the solution 406 to be investigated together with the enzyme 408 are hybridized with the immobilized DNA probe molecules 405, the biosensor 400 is rinsed, as a result of which the nonhybridized DNA strands are removed and the biosensor chip 400 is cleaned of the solution 406 to be investigated. The rinsing solution used for rinsing or a further solution supplied separately in a further phase has an electrically uncharged substance added to it, which contains molecules that can be cleaved by means of the enzyme 408 at the hybridized DNA strands 407, into a first partial molecule 410 and into a second partial molecule. One of the two molecules is redox-active.

As shown in FIG. 4C, the for example negatively charged first partial molecules 410 are attracted to the positively charged first electrode 401, which is indicated by means of the arrow 411 in FIG. 4C. The negatively charged first partial molecules 410 are oxidized at the first electrode 401, which has a positive electrical potential, and are attracted as oxidized partial molecules 413 to the negatively charged second electrode 402, where they are reduced again. The reduced partial molecules 414 again migrate to the positively charged first electrode 401. In this way, an electrical circulating current is generated, which is proportional to the number of charge carriers respectively generated by means of the enzymes 408.

The electrical parameter which is evaluated in this method is the change in the electric current m=dI/dt as a function of the time t, as is illustrated schematically in the diagram 500 in FIG. 5.

FIG. 5 shows the function of the electric current 501 depending on the time 502. The resulting curve profile 503 has an offset current $I_{offset}$ 504, which is independent of the temporal profile. The offset current $I_{offset}$ 504 is generated on account of non-idealities of the biosensor 400. An essential cause of the offset current $I_{offset}$ resides in the fact that the covering of the first electrode 401 with the DNA probe molecules 405 is not effected in an ideal manner, i.e. not completely densely. In the case of a completely dense coverage of the first electrode 401 with the DNA probe molecules 405, an essentially capacitive electrical coupling would result on account of the so-called double-layer capacitance, which is produced by the immobilized DNA probe molecules 405, between the first electrode 401 and the electrically conductive solution 406 to be investigated. However, the incomplete coverage leads to parasitic current paths between the first electrode 401 and the solution 406 to be investigated, which inter alia also have resistive components.

However, in order to enable the oxidation/reduction process, the coverage of the first electrode 401 with the DNA probe molecules 405 is intended not to be complete at all, in order that the electrically charged partial molecules, i.e. the negatively charged first partial molecules 410, can pass to the first electrode 401 on account of an electrical force and also as a result of diffusion processes. In order, on the other hand, to achieve the greatest possible sensitivity of such a biosensor, and in order simultaneously to achieve the least possible parasitic effects, the coverage of the first electrode 401 with DNA probe molecules 405 should be sufficiently dense. In order to achieve a high reproducibility of the measured values determined by means of such a biosensor 400, both electrodes 401, 402 are intended always to provide an adequately large area afforded for the oxidation/reduction process in the context of the redox recycling process.

Macromolecular biomolecules are to be understood for example as proteins or peptides or else DNA strands having a respectively predetermined sequence. If proteins or peptides are intended to be registered as macromolecular biomolecules, then the first molecules and the second molecules are ligands, for example active substances with a possible binding activity, which bind the proteins or peptides to be registered to the respective electrode on which the corresponding ligands are arranged.

Ligands that may be used are enzyme agonists, pharmaceuticals, sugars or antibodies or some other molecule which has the capability of specifically binding proteins or peptides.

If the macromolecular biomolecules used are DNA strands having a predetermined sequence which are intended to be registered by means of the biosensor, then it is possible, by means of the biosensor, for DNA strands having a predetermined sequence to be hybridized with DNA probe molecules having the sequence that is complementary to the sequence of the DNA strands as molecules on the first electrode.

A probe molecule (also called capture molecule) is to be understood as a ligand or a DNA probe molecule.

The value m=dI/dt introduced above, which corresponds to the gradient of the straight line 503 from FIG. 5, depends on the length and also the width of the electrodes used for registering the measurement current. Therefore, the value m is approximately proportional to the longitudinal extent of the electrodes used, for example in the case of the first electrode 201 and the second electrode 202 proportional to the length thereof perpendicular to the plane of the drawing in FIG. 2A and FIG. 2B. If a plurality of electrodes are connected in parallel, for example in the known interdigital electrode arrangement (cf. FIG. 3A, FIG. 3B), then the change in the measurement current is proportional to the number of electrodes respectively connected in parallel.

However, the value of the change in the measurement current may have a range of values that fluctuates to a very great extent, on account of various influences, the current range that can be detected by a sensor being referred to as the dynamic range. A current intensity range of five decades is often mentioned as a desirable dynamic range. Causes of the great fluctuations may be, in addition to the sensor geometry, also biochemical boundary conditions. Thus, it is possible that macromolecular biomolecules of different types to be registered will bring about greatly different ranges of values for the resulting measurement signal, i.e. in particular the measurement current and the temporal change thereof, which in turn leads to a widening of the required overall dynamic range with corresponding requirements for a predetermined electrode configuration with downstream uniform measurement electronics.

The requirements made of the large dynamic range of such a circuit have the effect that the measurement electronics are expensive and complicated in their configuration, in order to operate sufficiently accurately and reliably in the required dynamic range.

Furthermore, the offset current $I_{offset}$ is often much greater than the temporal change in the measurement current m over the entire measurement duration. In such a scenario, it is necessary, within a large signal, to measure a very small time-dependent change with high accuracy. This makes very high requirements of the measurement instruments used, which makes the registering of the measurement current complex, complicated and expensive. This fact is also at odds with a miniaturization of sensor arrangements that is striven for.

To summarize, the requirements made of the dynamic range and therefore of the quality of a circuit for detecting sensor events are extremely high.

It is known, during circuit design, to take account of the non-idealities of the components used (noise, parameter variations) in the form such that an operating point at which these non-idealities play a part that is as negligible as possible is chosen for these components in the circuit.

If a circuit is intended to be operated over a large dynamic range, maintaining an optimum operating point over all the ranges becomes increasingly more difficult, more complex and thus more expensive, however.

Small signal currents that are obtained at a sensor, for example, can be raised, with the aid of amplifier circuits to a level that permits the signal current to be forwarded for example to an external device or internal quantification.

A digital interface between the sensor and the evaluating system is advantageous for reasons of interference immunity and user-friendliness. Thus, the analog measurement currents are intended to be converted into digital signals actually in the vicinity of the sensor, which can be effected by means of an integrated analog-to-digital converter (ADC). Such an integrated concept for digitizing an analog small current signal is described in Uster, M., Loeliger, T., Guggenbühl, W., Jäckel, H. (1999) "Integrating ADC Using a Single Transistor as Integrator and Amplifier for Very Low (lfA Minimum) Input Currents", Advanced A/D and D/A Conversion Techniques and their Applications, Conference at the University of Strathclyde (Great Britain) Jul. 27–28, 1999, Conference Publication No. 466, pp. 86–89, IEE, for example.

In order to achieve the required dynamic range, the ADC should have a correspondingly high resolution and a sufficiently high signal-to-noise ratio. Integrating such an analog-to-digital converter in direct proximity to a sensor electrode furthermore constitutes a high technological challenge, and the corresponding process implementation is complex and expensive. Furthermore, achieving a sufficiently high signal-to-noise ratio in the sensor is extremely difficult.

SUMMARY OF THE INVENTION

The invention is based on the problem of providing an error-robust circuit arrangement with an improved detection sensitivity for electric currents that are very weakly variable with respect to time.

The problem is solved by means of a circuit arrangement, an electrochemical sensor, a sensor arrangement and a method for processing a current signal provided via a sensor electrode having the features in accordance with the independent patent claims.

An embodiment of the invention provides a circuit arrangement having a sensor electrode, having a first circuit unit, which is electrically coupled to the sensor electrode, and having a second circuit unit, which has a first capacitor. The first circuit unit is set up in such a way that it holds the electrical potential of the sensor electrode in a predeterminable first reference range around a predeterminable electrical desired potential by coupling the first capacitor and the sensor electrode in such a way that a matching of the electrical potential is made possible. The second circuit unit is set up in such a way that, if the electrical potential of the first capacitor is outside a second reference range, said second circuit unit detects this event and brings the first capacitor to a first electrical reference potential.

The functionality of the circuit arrangement according to an embodiment of the invention is explained clearly below. The circuit arrangement of the embodiment of the invention has a sensor electrode at which a sensor event may take place. By way of example, a hybridization event between DNA half strands contained in a liquid to be investigated and capture molecules immobilized on the sensor electrode may be effected at the sensor electrode. If the molecules to be registered have an enzyme label, for example, which generates free electrical charge carriers in the liquid to be investigated, then an electric current signal to be detected flows proceeding from the sensor electrode into the circuit arrangement of an embodiment of the invention. The first circuit unit of the circuit arrangement is set up in such a way that this clearly holds the electrical potential of the sensor electrode within a first reference range. As long as the electrical potential of the sensor electrode is within said reference range, the first circuit unit decouples the sensor electrode from a capacitor of the second circuit unit. If the electrical potential of the sensor electrode moves outside the first reference range, then the first circuit unit produces a gradual electrical coupling between the sensor electrode and the first capacitor of the second circuit unit. A matching of the electrical potential of the sensor electrode to that of the first capacitor of the second circuit unit is made possible on account of said electrical coupling. Clearly, free electrical charges can flow back and forth between the capacitor and the sensor electrode, in such a way that the electrical potential of the sensor electrode is brought back into the first reference range. As a result, small quantities of charge can be progressively shifted proceeding from the sensor electrode onto the second capacitor of the second circuit unit, or vice versa. Clearly, small sensor currents are integrated up to form a charge packet on the capacitor until the charge packet has a predetermined sufficient size to be detected. Therefore, the quantity of charge situated on the first capacitor of the second circuit unit changes in a manner characteristic of the number of sensor events effected on the sensor electrode. In other words, the first capacitor of the second circuit unit subsequently supplies to the sensor electrode that quantity of charge which flows away from the sensor electrode on account of the sensor events. Therefore, the first circuit unit and the capacitor function inter alia in a manner similar to a potentiostat, by holding the electrical voltage of the sensor electrode within the first reference range, preferably at the electrical desired potential.

However, if the electrical potential of the first capacitor moves outside the second reference range on account of the charge carriers exchanged with the sensor electrode, then this event is detected by the second circuit unit, and the second circuit unit ensures that the first capacitor is brought to a first electrical reference potential. To put it clearly, the second circuit unit forms the following functionality: if a sufficiently large quantity of charge has been taken from the first capacitor by the sensor electrode (or conversely if a sufficiently large quantity of charge has flowed from the sensor electrode onto the first capacitor), this event is detected by the second circuit unit for example by outputting of a pulse. Furthermore, the electrical charge that has flowed away onto the sensor electrode is subsequently supplied to the first capacitor (or the electrical charge that has flowed from the sensor electrode onto the first capacitor is taken from the first capacitor) in order to return the capacitor again to a defined operating point, i.e. to the first electrical reference potential.

The circuit arrangement according to an embodiment of the invention having the functionality described is suitable for registering extremely small analog electric current signals and converting them into a digital signal, i.e. a sequence of temporally successive, separate pulses. The analog measurement signal is digitized in direct spatial proximity to the sensor electrode, thereby largely avoiding parasitic, additional noise on account of a temporally as well as spatially long communication path of an analog signal. Therefore, the circuit arrangement according to an embodiment of the invention has a high signal-to-noise ratio when registering electric currents.

The circuit arrangement according to an embodiment of the invention is suitable in particular for detecting a progressively rising current signal generated in accordance with the redox recycling principle (cf. FIG. 5). By means of suitable setting of the measurement time or the reference ranges of the electrical potential of the sensor electrodes and of the first capacitor which are relevant to the functionality of the circuit arrangement according to an embodiment of the invention, the number of events to be detected (e.g. in the form of pulses) can be set flexibly to the requirements of the individual case.

Preferably, the circuit arrangement has a counter element that is electrically coupled to the second circuit unit and is set up in such a way that it counts the number and/or the temporal sequence of the events. Furthermore, the circuit arrangement may be set up in such a way that a direct outputting of the sensor frequency, i.e. the frequency of the events, is provided.

In accordance with an advantageous development, the counter element is set up in such a way that it registers the temporal sequence of the events in at least two time intervals at a temporal distance from one another.

In other words, the events detected by the second circuit unit in respect of the fact that the electrical potential of the first capacitor moves outside the second reference range are counted by means of the counter element, and in particular the temporal distance between successive events is detected. Counting the temporal distances between the events corresponds to determining the frequency of the events. This means that the analog current signal on the sensor electrode is converted into a digital signal that is contained in the frequency determined. As a result, it is possible, in particular, to achieve a high dynamic range of the circuit arrangement. Technically, it is possible, with a tenable outlay, to generate, detect and process for example frequencies of between 100 Hz and 10 MHz, so that a dynamic range of five or more decades can be achieved.

Preferably, the circuit arrangement according to an embodiment of the invention has a calibration device that can be coupled to the first circuit unit and serves for calibrating the circuit arrangement, which is set up in such a way that a second electrical reference potential can be applied to the first circuit unit by means of the calibration device, the first circuit unit being coupled either to the calibration device or to the sensor electrode.

The possibility of being able, according to an embodiment of the invention, to calibrate the circuit arrangement increases the degree of reliability of the signals registered and enables monitoring of the entirely satisfactory functionality of the circuit arrangement. Furthermore, the measurement accuracy of the circuit arrangement can be increased by means of a calibration device.

Preferably, the first circuit unit has a first comparator element having two inputs and an output, the first input being coupled to the sensor electrode in such a way that the first input is at the electrical potential of the sensor electrode, whereas the second input is brought to a third electrical reference potential, which defines the electrical desired potential. The first comparator element is set up in such a way that an electrical signal is generated at its output such that the electrical potential of the sensor electrode is held in the predeterminable first reference range around the predeterminable electrical desired potential.

The first circuit unit serves for holding constant a predeterminable voltage, referred to here as the electrical desired potential, at the sensor electrodes.

In accordance with an advantageous refinement in the case of the circuit arrangement, the first circuit unit has a variable nonreactive resistor, by means of which the sensor electrode can be coupled to the first capacitor of the second circuit unit in such a way that the potential of the sensor electrode is held in the predeterminable first reference range around the predeterminable electrical desired potential.

In other words, for the purpose of holding the potential of the sensor electrode constant, the coupling of the sensor electrode to the first capacitor may be realized by means of a controllable nonreactive resistor. The value of the nonreactive resistance that is presently set in each case is a measure of the present strength of the electrical coupling between the sensor electrode and the first capacitor.

Furthermore, the first circuit unit preferably has a transistor, the gate region of which is coupled to the output of the first comparator element, the first source/drain region of which is coupled to the sensor electrode and the second source/drain region of which is coupled to the first capacitor.

In other words, the transistor described functions as a control element that sets the current flow between the sensor electrode and the first capacitor.

Furthermore, the second circuit unit may have a second comparator element having two inputs and an output, the first input being coupled to the first capacitor in such a way that the first input is at the electrical potential of the first capacitor; the second input being at a fourth electrical reference potential, which defines the second electrical reference range. The second comparator element is set up in such a way that an electrical signal is generated at its output such that, if the electrical potential of the first capacitor exceeds the fourth electrical reference potential, the first capacitor is brought to the first electrical reference potential.

As an alternative to the refinement described, the second circuit unit of the circuit arrangement has a second comparator element having two inputs and an output, the first input being coupled to the first capacitor in such a way that the first input is at the electrical potential of the first capacitor, the second input being at a fourth electrical reference potential, which defines the second electrical reference range. Furthermore, the second comparator element is set up in such a way that an electrical signal is generated at its output such that, if the electrical potential of the first capacitor falls below the fourth electrical reference potential, the first capacitor is brought to the first electrical reference potential.

The first and/or the second comparator element is preferably an operational amplifier.

The above explanations show that the elements for forming the circuit arrangement according to an embodiment of the invention are all electronic standard components which are expedient in production and which can be produced by standard methods. Therefore, the circuit arrangement according to an embodiment of the invention can be produced with little complexity.

In accordance with a preferred development of the circuit arrangement according to an embodiment of the invention, its second circuit unit has at least one second capacitor, the circuit arrangement being set up in such a way that either one of the at least one second capacitors or the first capacitor or at least two of the capacitors is/are simultaneously connected into the circuit arrangement.

Clearly, the circuit arrangement has a plurality of parallel-connected capacitors which have different or identical material parameters (for example capacitance C) and in each case one or a plurality of which can optionally be actively connected into the circuit arrangement. A user therefore has the possibility of selecting, in accordance with the requirements of the individual case, that or those suitable capacitors which is or are expedient with regard to measurement accuracy and desired dynamic range. Providing different capacitors, each of which can be actively connected into the circuit arrangement, increases the detection sensitivity of the circuit arrangement for registering electric currents, and likewise increases the dynamic range.

The circuit arrangement according to an embodiment of the invention may be designed as an integrated circuit.

In particular, the circuit arrangement of an embodiment of the invention may be integrated into a semiconductor substrate (e.g. a chip of a silicon wafer), or be formed partially on the semiconductor substrate. The integration of the circuit arrangement increases the sensitivity and miniaturizes the circuit arrangement. Miniaturization brings about a cost advantage since macroscopic measurement equipment is obviated. Furthermore, the circuit arrangement according to an embodiment of the invention can be produced by means of standardized semiconductor technology methods which likewise has a favorable effect on the production costs. Furthermore, the integration of the circuit arrangement into a semiconductor substrate enables the current signal that is to be registered to be processed on chip, i.e. in direct proximity to the sensor event. Short communication paths of the current signal keep down interference influences such as noise, etc., so that a high signal-to-noise ratio can be achieved.

An embodiment of the invention furthermore provides an electrochemical sensor having a circuit arrangement having the features described. The electrochemical sensor may be configured in particular as a redox recycling sensor.

As described above with reference to FIG. 4A, FIG. 4B, FIG. 4C, a sensor based on the principle of redox recycling has a sensor current characteristic that rises progressively with respect to time. Such a current signal that rises essentially monotonically with respect to time is well suited to being registered by means of the circuit arrangement according to an embodiment of the invention, since the progressively increasing current signal can be decomposed into charge packets that have accumulated on the first capacitor and are detected by means of pulses individually by the circuit arrangement according to an embodiment of the invention. In particular, the detection sensitivity of the circuit arrangement according to an embodiment of the invention is high enough to register electric currents of the order of magnitude of between approximately 1 pA and approximately 100 nA, as are often generated by biosensors in accordance with the redox recycling principle with customary sensor electrode geometries.

Furthermore, an embodiment of the invention provides a sensor arrangement having a plurality of circuit arrangements having the features described above.

What is possible, therefore, is a parallel analysis, for example the parallel registering of different DNA half strands by means of a plurality of redox recycling sensors that have different capture molecules immobilized on their sensor electrodes. A parallel analysis of a liquid to be investigated is an urgent requirement with regard to many applications in biotechnology and genetic engineering or in foodstuffs technology. A temporally parallel analysis saves time and therefore costs. Furthermore, the sensor arrangement may be set up in such a way that the individual sensor cells (formed in each case by a circuit arrangement) can be read serially.

In particular, in the case of the sensor arrangement, each of the circuit arrangements may be set up as an autonomously operating sensor element.

The circuit arrangements of the sensor arrangement may be arranged essentially in matrix form, but as an alternative also e.g. hexagonally.

Furthermore, the sensor arrangement may have a central drive circuit for driving a circuit arrangement, a central supply circuit for providing supply voltages or supply currents and/or a central read-out circuit for reading the circuit arrangements. This circuit or these circuits are preferably coupled to at least one portion of the circuit arrangements.

The method according to an embodiment of the invention for processing a current signal provided via a sensor electrode is described below. Refinements of the circuit arrangement, of the electrochemical sensor and of the sensor arrangement also apply to the method for processing a current signal provided via a sensor electrode.

The method according to an embodiment of the invention for processing a current signal provided via a sensor electrode is effected using a circuit arrangement according to an embodiment of the invention having the features described above. In accordance with the method, the electrical potential of the sensor electrode is held in the predeterminable first reference range around the predeterminable electrical desired potential by the first capacitor and the sensor electrode being coupled in such a way that a matching of the electrical potential is made possible. Furthermore, if the electrical potential of the first capacitor moves outside the second reference range, by means of the second circuit unit, this event is detected and the first capacitor is brought to the first electrical reference potential.

In accordance with a preferred development of the method according to an embodiment of the invention, the number and/or the temporal sequence of the events is counted by means of a counter element electrically coupled to the second circuit unit.

Preferably, the counter element is used to register the temporal sequence of the events in at least two time intervals at a temporal distance from one another.

BRIEF DESCRIPTION OF THE DRAWINGS

Exemplary embodiments of the invention are illustrated in the figures and are explained in more detail below.

FIG. 1 shows a schematic view of a circuit arrangement in accordance with a first exemplary embodiment of the invention;

FIG. 6B shows a schematic view of a circuit arrangement in accordance with a third exemplary embodiment of the invention;

FIG. 8 shows a block diagram showing the construction of a first circuit unit (voltage regulator) shown in FIG. 7;

FIG. 12 shows a preferred exemplary embodiment of the sensor arrangement according to the invention.

DETAILED DESCRIPTION OF PREFERRED EMBODIMENTS OF THE INVENTION

Figure 2A:
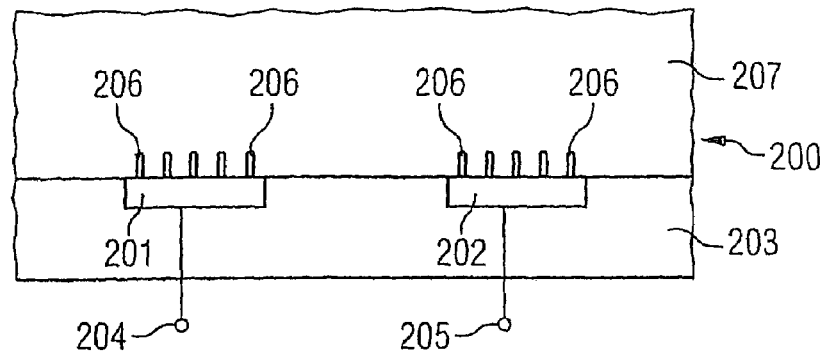
FIG. 2A shows a cross-sectional view of a sensor in accordance with the prior art in a first operating state.
Figure 2B:
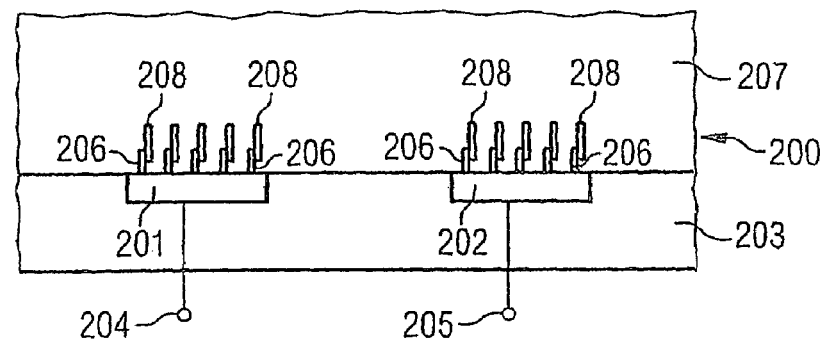
FIG. 2B shows a cross-sectional view of the sensor in accordance with the prior art in a second operating state.
Figure 3A:
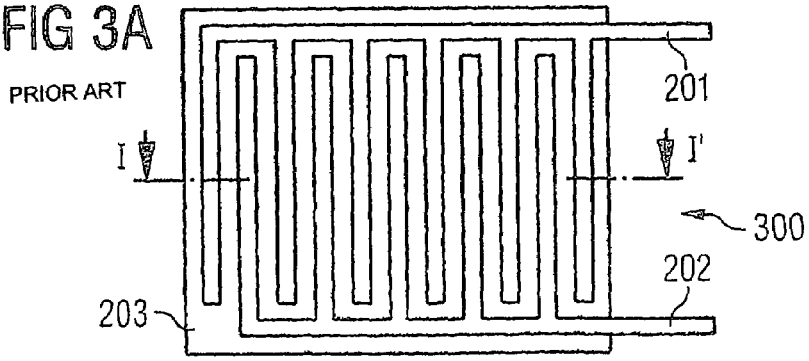
FIG. 3A shows a plan view of interdigital electrodes in accordance with the prior art.
Figure 3B:
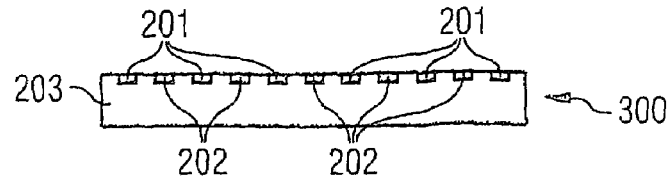
FIG. 3B shows a cross-sectional view along the section line I–I' of the interdigital electrodes in accordance with the prior art as shown in FIG. 3A.

A first preferred exemplary embodiment of the circuit arrangement according to the invention is described below with reference to FIG. 1.

The circuit arrangement 100 shown in FIG. 1 has a sensor electrode 101, a first circuit unit 102, which is electrically coupled to the sensor electrode 101, and a second circuit unit 103, which has a first capacitor 104. The first circuit unit 102, illustratively a potentiostat, is set up in such a way that it holds the electrical potential of the sensor electrode 101 in a predeterminable first reference range around a predeterminable electrical desired potential by coupling the first capacitor 104 and the sensor electrode 101 in such a way that a matching of the electrical potential is made possible (by means of a current flow for control). Furthermore, the second circuit unit 103 is set up in such a way that, if the electrical potential of the first capacitor 104 is outside a second reference range, said second circuit unit detects this event and brings the first capacitor 104 to a first electrical reference potential.

As is furthermore shown in FIG. 1, capture molecules 105 are immobilized on the surface of the sensor electrode 101. The capture molecules 105 from FIG. 1 have hybridized with molecules 106 to be registered, each of the molecules 106 to be registered having an enzyme label 107.

Figure 4A:
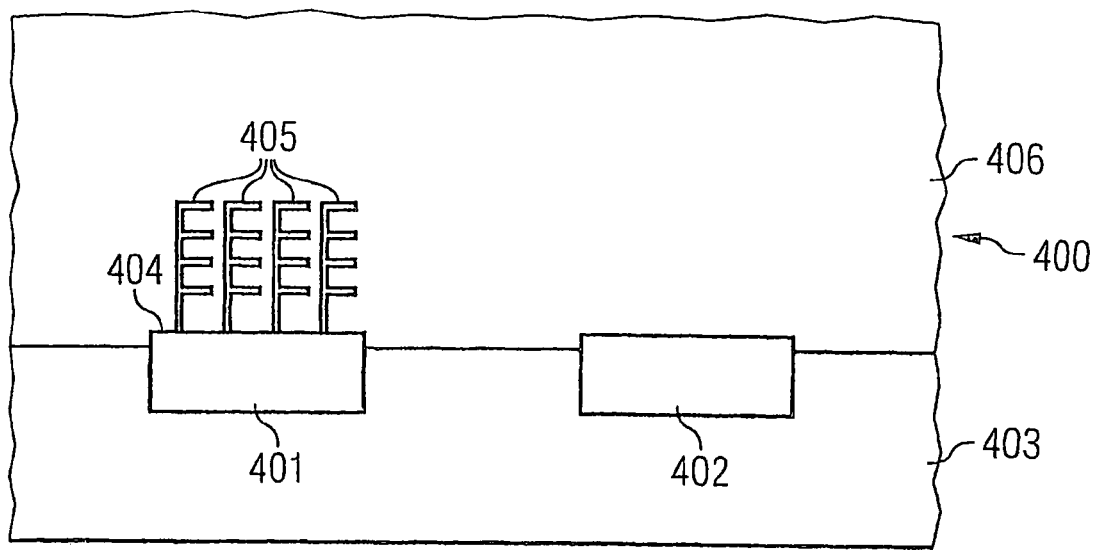
FIG. 4A shows a biosensor based on the principle of redox recycling in a first operating state in accordance with the prior art.
Figure 4B:
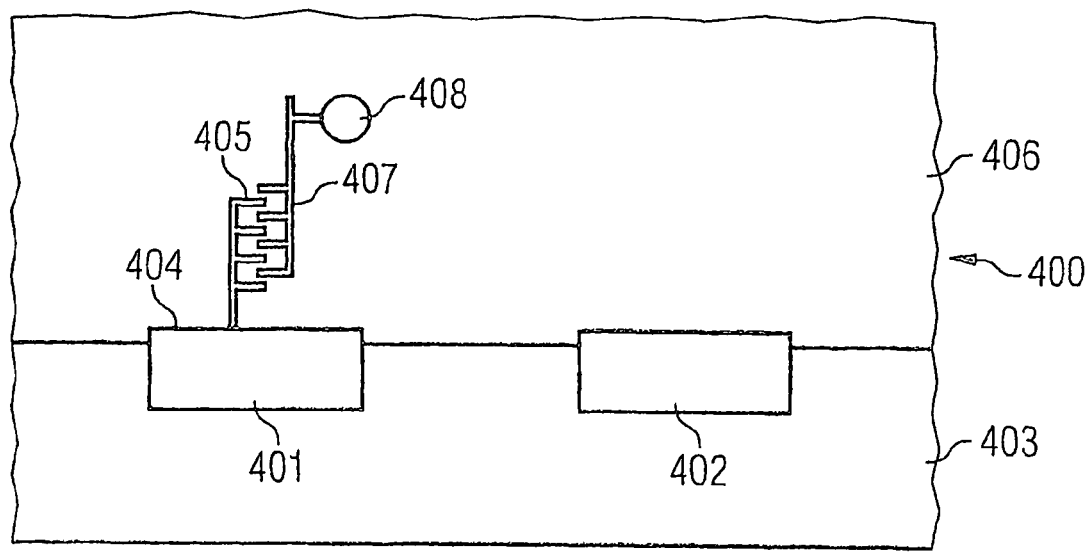
FIG. 4B shows a biosensor based on the principle of redox recycling in a second operating state in accordance with the prior art.
Figure 4C:
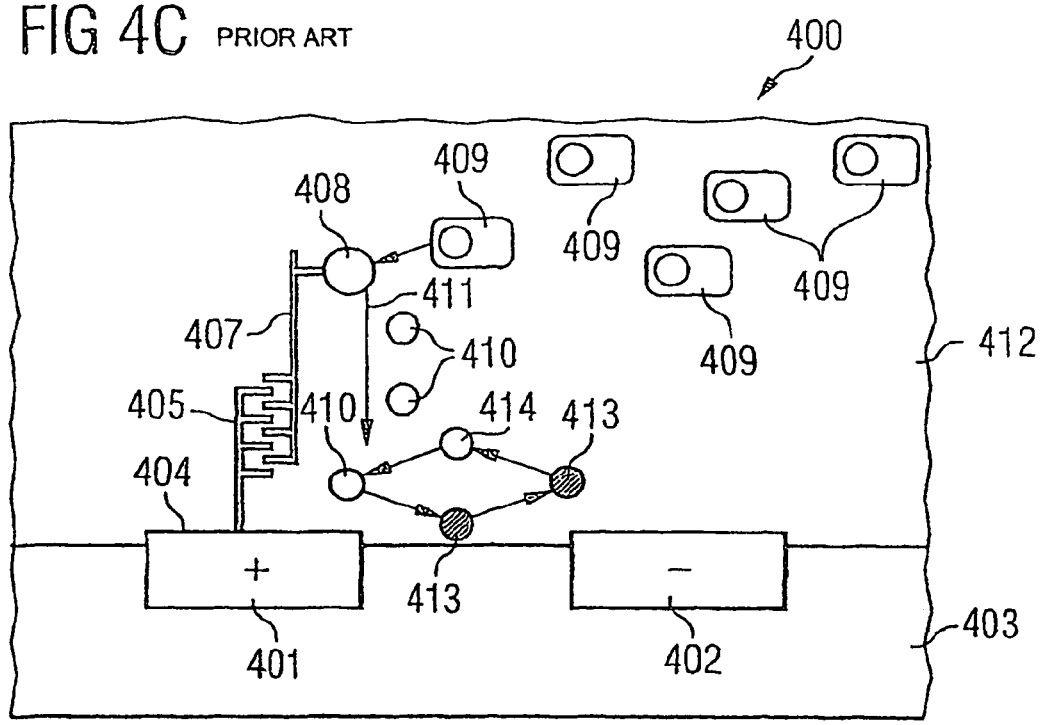
FIG. 4C shows a biosensor based on the principle of redox recycling in a third operating state in accordance with the prior art.

The sensor electrode 101 with the capture molecules immobilized thereon as shown in FIG. 1 functions according to the principle of redox recycling (cf. FIG. 4A, FIG. 4B, FIG. 4C). Therefore, FIG. 1 shows electrically charged particles 108, which are generated by means of the enzyme label 107 in the liquid to be investigated and which generate an electric sensor current that is coupled into the circuit arrangement 100 from the first sensor electrode 101.

This sensor current alters the electrical potential of the sensor electrode 101 in a characteristic manner. This electrical potential is present at the input of a first control unit 109 of the first circuit unit 102. The first circuit unit 102 and in particular the first control unit 109 ensure that the sensor electrode 101 remains at a predeterminable, constant electrical potential by carrying out a shift of charge carriers between the first capacitor 104 and the sensor electrode 101 when there is a sufficient great deviation of the sensor electrode potential from the electrical desired potential. This is indicated schematically in FIG. 1 by means of the controllable nonreactive resistor 110, which can be controlled by the first control unit 109. The circuit block shown is an analog control loop that controls the current flow between the capacitor 104 and the sensor electrode 101 in such a way that the voltage at the sensor electrode 101 remains constant. A continuous control of the current flow is made possible by means of the controllable resistor 110. If the electrical potential of the sensor electrode 101 moves outside the first reference range on account of a sufficiently large number of sensor events at its surface, then the first circuit unit 102 and in particular the first control unit 109 ensure that the current flow between the sensor electrode 101 and the first capacitor 104 increases or decreases, thereby enabling a matching of the electrical potential between the first capacitor 104 and the sensor electrode 101. Clearly, the resistance of the controllable resistor 110 is thus increased or decreased by means of the first control unit 109 of the first circuit unit 102, thereby enabling a current flow between the sensor electrode 101 and the first capacitor 104. In this scenario, electrical charge can flow back and forth between the first capacitor 104 and the sensor electrode 101.

If the electrical potential of the first capacitor 104 moves outside a second reference range on account of this charge shift, then this event is detected by the second circuit unit 103 and in particular by a second control unit 111, which preferably has a comparator, of the second circuit unit 103. As shown in FIG. 1, this detection may consist in an electrical pulse 112 being generated at an output of the second control unit 111.

Furthermore, if the electrical potential of the first capacitor 104 moves outside the second reference range, the first capacitor 104 is brought to the first electrical reference potential by means of the second circuit unit 103 and in particular by means of the second control unit 111 of the second circuit unit 103. This is indicated in FIG. 1 in that a further switch 113 is closed on account of a signal initiated by the second control unit 111 of the second circuit unit 103, as a result of which the first capacitor 104 is electrically coupled to a voltage source 114, as a result of which the first capacitor 104 is brought to the first electrical reference potential defined by means of the voltage source 114.

A basic idea of the circuit arrangement according to the invention may clearly be seen in the fact that a sensor current to be registered is converted into a frequency proportional to the current without prior analog amplification. By means of the circuit arrangement according to the invention, the potential at the sensor electrode is held constant and the electrical charge required for this (having a positive or negative sign) is drawn from a capacitor having the capacitance C. Owing to the charge drawn ΔQ $$\Delta Q = \int I dt \quad (1)$$

on account of a current flow I between the first capacitor and the sensor electrode integrated over the time t, the voltage ΔU present at the first capacitor changes in accordance with the relationship $$\Delta Q = C \Delta U \quad (2)$$

The voltage present at the capacitor is monitored by means of a threshold value circuit. If a specific value is exceeded or undershot, then the circuit initiates a digital pulse by means of which a switch is closed, as a result of which the electrical voltage at the capacitor is reset to a predetermined value. What is obtained as a result, in measurement operation, is a pulse sequence from the threshold value circuit whose frequency is proportional to the signal current.

As described above with reference to FIG. 1, the circuit arrangement according to the invention, for operating an electrochemical sensor, essentially has two circuit units. The first circuit unit monitors the electrical potential (i.e. the voltage with respect to a reference point) present at the sensor electrode. By way of example, an operational amplifier may be used to compare the electrical potential of the sensor electrode with a reference potential, and to control the electric current flow between the sensor electrode and the first capacitor in such a way that the electrical potential of the sensor electrode remains constant.

The counter-current required for matching the sensor current is drawn, as described, from the first capacitor of the second circuit unit. The voltage at the first capacitor is monitored by a threshold value circuit, for example a comparator circuit, in the second circuit unit. In the case where a second reference range of the electrical potential of the first capacitor is exceeded or undershot, the second circuit unit outputs a reset pulse. This digital pulse, which preferably has a fixed temporal length, resets the potential of the capacitor (or the electrical voltage between the two capacitor plates) to a first electrical reference potential. The pulse should have a constant length since the counter-current is drawn from a voltage source during this time. This dead time reduces the measured frequency and, insofar as the dead time is not negligibly short, has to be taken into account in the evaluation of the data.

In order, in a scenario in which the dead time is not negligible or is intended to be compensated for, to minimize the measurement error as a result of the resetting of the circuit, it is possible to provide two (or more) capacitors that are operated alternately in the manner described. If one (active) capacitor is charged by the sensor current, then the other (passive) capacitor is reset to the first electrical reference potential in this time interval. If the potential at the active capacitor exceeds the predetermined value, then, preferably, a reset pulse is not initiated immediately by the second circuit unit 103, rather firstly a changeover is made between the two capacitors and only afterward is the now passive capacitor reset. By means of this procedure, the sensor current is not drawn directly from a voltage source at any point in time, but rather always from a capacitor that serves as a charge reservoir.

Referring to FIG. 1 again, the reset process is preferably effected by means of a switching transistor that discharges (for example completely discharges) the first capacitor to a predeterminable potential in the reset phase. The first electrical reference potential is preferably a ground potential. The sensor current subsequently charges the first capacitor again. The temporal dependence of the electrical voltage at the first capacitor can be described by the following expression:

$$U(t) = 1/C \int_0^t I_{Sensor} dt' \qquad (3)$$

The sensor current $I_{sensor}$ derived from the sensor electrode has, as described above with reference to FIG. 5 a constant offset component $I_{offset}$ and a signal current that rises (ideally) linearly with time:

$$I_{sensor} = I_{offset} + mt \qquad (4)$$

If equation (4) is inserted into equation (3) and the integral is calculated, then the electrical voltage which builds up between a first instant $t_1$ and a second instant $t_2$ turns out to be:

$$U(t)=1/C \ (I_{offset}[t_2-t_1]+m/2[t_2^2-t_1^2]) \qquad (5)$$

The time interval $\Delta t$ in which a specific voltage difference $\Delta U$ is built up is therefore:

$$\Delta t = t_2 - t_1 = (C\Delta U)/(I_{offset}+m\bar{t}) \qquad (6)$$

In this case, $\bar{t}$ is the mean time of the interval considered, i.e.:

$$\bar{t}=(t_1+t_2)/2 \qquad (7)$$

The frequency f measured within a sufficiently short interval $\Delta t$ disregarding a dead time $t_{dead}$ during resetting of the capacitor ($t_{dead} \ll \Delta t$) accordingly turns out to be:

$$f=\Delta t^{-1}=I_{offset}/(C\Delta U)+m\bar{t}/(C\Delta U) \qquad (8)$$

This frequency f may be conducted away as a digital signal directly from the circuit arrangement (for example from a chip if the circuit arrangement is integrated into a semiconductor substrate) and be processed further and evaluated. Equation (8) shows that the frequency f has a constant component attributed to the offset current $I_{offset}$ of the sensor electrode. The second term in (8) represents the frequency component that rises linearly with time (the assumption of a current signal that rises exactly linearly is idealizing, of course), is attributed to sensor events in accordance with the redox recycling principle, and comprises the actual measurement variable m.

The metrologically relevant variable m is obtained by carrying out for example two period or frequency measurements with a predetermined time distance $\Delta t_{meas}=t_B-t_A$. If $t_A$ and $t_B$, respectively, are inserted into equation (8) and the frequencies $f_A$ and $f_B$ obtained therefrom are subtracted from one another, then the frequency difference $\Delta f$ obtained is:

$$\Delta f = f_B - f_A = m\Delta t_{meas}/(C\Delta U) \qquad (9)$$

The metrologically relevant variable m results from this as:

$$m = \Delta f C \Delta U / \Delta t_{meas} \qquad (10)$$

Figure 5:
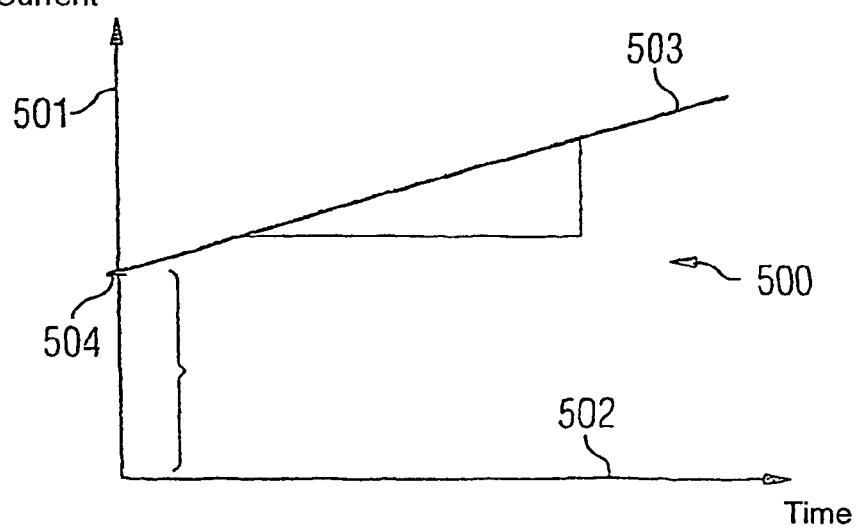
FIG. 5 shows a functional profile of a sensor current in the context of a redox recycling process.

Accordingly, from two measurements of the output frequency of the sensor, it is possible to directly determine the metrologically relevant variable m, clearly the gradient of the current-time curve profile 503 from FIG. 5.

As an alternative to the frequency or period duration measurement described, it is possible for the pulses of the second circuit unit to be provided to the input of a counter element that sums the number or the temporal sequence of the pulses and preferably converts this into a binary word coding the number of elapsed time intervals $\Delta t$.

Such a counter element may count the reset pulses of the first capacitor for a predetermined length of time, digitally output the counter reading after an external pulse and then reset the counter element.

The counter reading n of the counter element of the circuit arrangement after the time period $t_{count}=t_{c2}-t_{c1}$ defined by means of the instants $t_{c1}$ and $t_{c2}$ has elapsed is calculated to a good approximation as:

$$n = \int_{tc1}^{tc2} f \, dt = I_{offset}(t_{c2}-t_{c1})/(C\Delta U) + m(t_{c2}^2 - t_{c1}^2)/(2C\Delta U) \qquad (11)$$

In accordance with the explanations above referring to the determination of m from frequency measurements, at least two measurements of the counter readings n are necessary, from which both $I_{offset}$ and the metrologically relevant variable m can be determined by means of equation (11).

One advantage of integrating a counter element into the circuit arrangement of the invention is the resultant temporal averaging of the measurement result that is effected automatically. Since, in the case of the small sensor currents that are to be expected—particularly in the detection of biomolecules—, fluctuations in the instantaneous value of the measurement variable are possible (for example owing to noise effects, etc.), an averaging is particularly advantageous.

In accordance with a preferred exemplary embodiment of the circuit arrangement according to the invention, the second circuit unit has at least one second capacitor, the circuit arrangement being set up in such a way that either one of the at least one second capacitors or the first capacitor or at least two of the capacitors is/are simultaneously connected into the circuit arrangement.

In order to extend the dynamic range and in order to improve the measurement accuracy, provision is made, illustratively, of a storage capacitance that can be changed over. If the sensor electrode supplies an increased electric sensor current, which would result in an increased output frequency, a further capacitor, for example, may be connected in parallel with the first capacitor. This reduces the output frequency and thus possible measurement inaccuracies on account of the dead time during resetting of the first capacitor. In addition to the measurement range switching realized in this way, it is also possible to vary the interval $\Delta U$ within which the capacitor voltage oscillates. This permits a continuous tuning of the measurement range.

A circuit arrangement 600 in accordance with a second preferred exemplary embodiment of the invention is described below with reference to FIG. 6A.

The circuit arrangement 600 has a sensor electrode 601, a first circuit unit 602, which is coupled to the sensor electrode 601, and a second circuit unit 603, which has a first capacitor 604. The first circuit unit 602 is set up in such a way that it holds the electrical potential of the sensor electrode 601 in a predeterminable first reference range around a predeterminable electrical desired potential by coupling the first capacitor 604 and the sensor electrode 601 in such a way that a matching of the electrical potential is made possible. Furthermore, the second circuit unit 603 is set up in such a way that, if the electrical potential of the first capacitor 604 is outside a second reference range, said second circuit unit detects this event and brings the first capacitor 604 to a first electrical reference potential, provided by the first voltage source at the node 605, of the second circuit unit 603.

Furthermore, the circuit arrangement 600 has a counter element 606, which is electrically coupled to the second circuit unit 603 and is set up in such a way that it counts the number and the temporal sequence of the events.

Furthermore, the first circuit unit 602 has a first comparator element 607 having two inputs and an output, the first input being coupled to the sensor electrode 601 in such a way that the first input is at the electrical potential of the sensor electrode 601. The second input is brought to a third electrical reference potential, which defines the electrical desired potential (or the first electrical reference range) The third electrical reference potential, the potential of the second input of the first comparator element 607, is provided by a second voltage source 608. Furthermore, the first comparator element 607 is set up in such a way that an electrical signal is generated at its output such that the electrical potential of the sensor electrode 601 is held in the predeterminable first reference range around the predeterminable electrical desired potential.

Figure 6A:
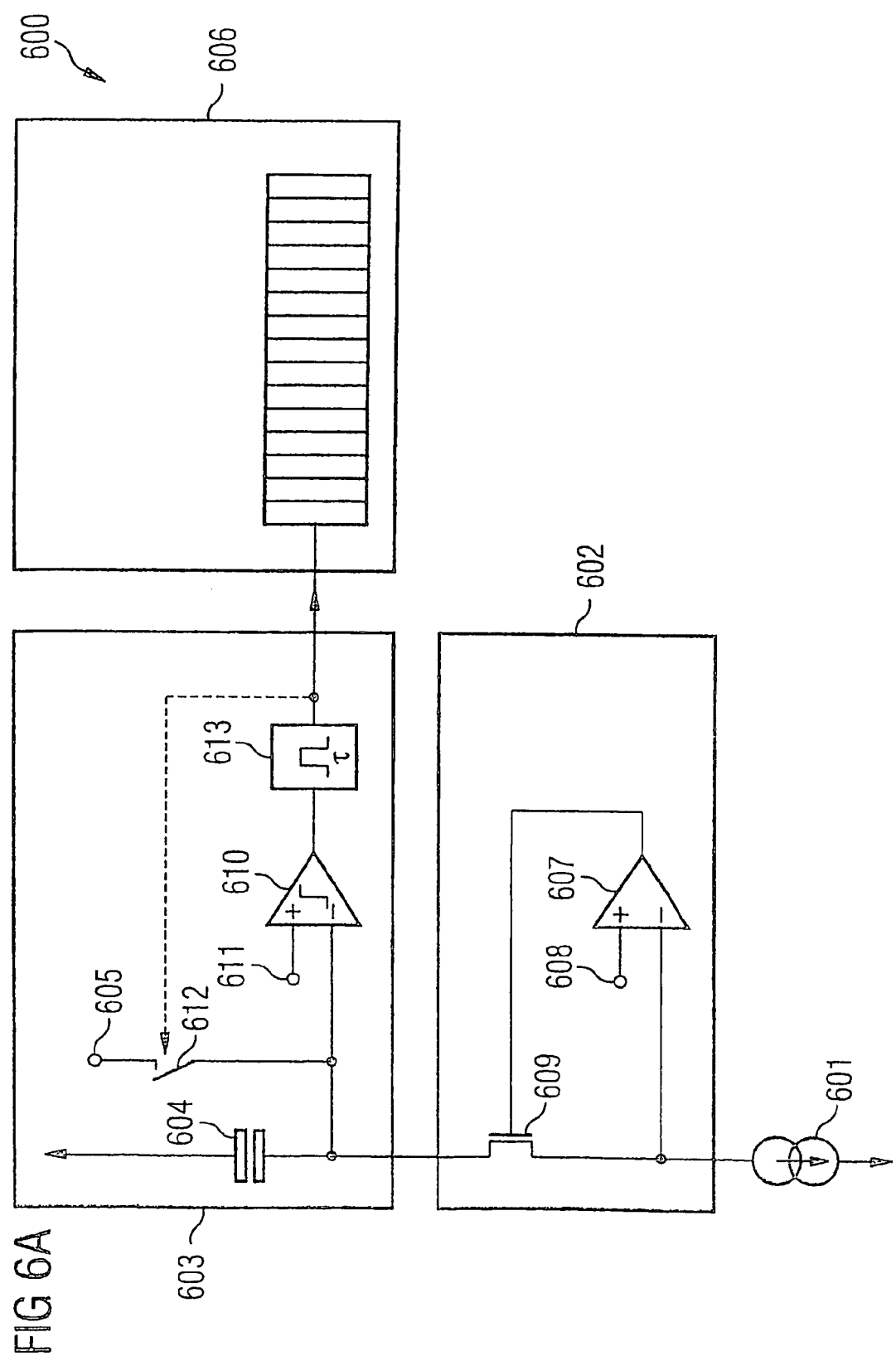
FIG. 6A shows a schematic view of a circuit arrangement in accordance with a second exemplary embodiment of the invention.

As is furthermore shown in FIG. 6A, the first circuit unit 602 has a transistor 609, the gate region of which is coupled to the output of the first comparator element 607, the first source/drain region of which is coupled to the sensor electrode 601 and the second source/drain region of which is coupled to the first capacitor 604.

Clearly, the field-effect transistor 609 is a variable nonreactive resistor (controllable by the first comparator element 607) by means of which the sensor electrode 601 can be coupled to the first capacitor 604 of the second circuit unit 603 in such a way that the electrical potential of the sensor electrode 601 is held in the predeterminable first reference range around the predeterminable electrical desired potential. In other words, any intermediate value between complete coupling and complete decoupling of sensor electrode 601 and capacitor 604 can be set by means of the transistor 609.

Furthermore, the second circuit unit 603 has a second comparator element 610 having two inputs and an output, the first input being coupled to the first capacitor 604 in such a way that the first input is at the electrical potential of the first capacitor 604, and the second input being at a fourth electrical reference potential provided by a third voltage source 611, which fourth electrical reference potential defines the second electrical reference range. The second comparator element 610 is set up in such a way that an electrical signal is generated at its output such that, if the electrical potential of the first capacitor 604 exceeds the fourth electrical reference potential, the first capacitor 604 is brought to the first electrical reference potential. For this purpose, the second circuit unit 603 provides the switch 612 (which may be designed as a transistor, for example) with an electrical signal such that the switch 612 is closed and an electrical coupling is produced between the first voltage source 605 and the first capacitor 604.

Furthermore, a pulse transmitter 613 is connected to the output of the second comparator 610, and detects the event that the electrical potential of the first capacitor 604 is outside the second reference range, and outputs a digital pulse having a defined length $\tau$.

As is furthermore shown in FIG. 6A, this pulse signal of the pulse transmitter 613 is provided to the counter element 606, which counts the number of pulses and the temporal sequence thereof (i.e. the frequency at which the pulses arrive).

The first comparator element 607 and the second comparator element 610 of the circuit arrangement 600 are in each case configured as an operational amplifier.

The basic circuit diagram of the circuit arrangement 600 according to the invention as shown in FIG. 6A thus has a potentiostat unit realized by means of the first circuit unit 602 and by means of the first capacitor 604, respectively. This holds the electrical potential of the sensor electrode 601 at the electrical desired potential in the first reference range, defined by means of the third electrical reference potential. The sensor current derived from the sensor electrode 601 is drawn from the second circuit unit 603, which furthermore functions as a current-frequency converter. The first capacitor 604 subsequently supplies electrical charge to the sensor electrode 601 for the purpose of holding the electrical potential thereof, the electrical voltage present at the first capacitor 604 being monitored by means of the comparator circuit described. If the electrical voltage of the first capacitor 604 falls below a threshold value, then the second comparator element 610 or the pulse transmitter 613 initiates a pulse having the defined length $\tau$, which, by means of the switch 612, subjects the first capacitor 604 to charge reversal to the electrical potential of the first voltage source 605. The pulse furthermore serves as a counting pulse for the counter element 606 coupled to the output of the second comparator element 610.

It must be emphasized that the circuit arrangement 600 shown in FIG. 6A is set up in such a way that it provides the sensor electrode 601 with electric currents; the sensor electrode 601 in this case operates as a current sink. By contrast, if electric currents generated at the sensor electrode 601 are intended to be taken up by the circuit arrangement 600, the latter would have to be constructed complementarily.

A third preferred exemplary embodiment of the circuit arrangement according to the invention is described below with reference to FIG. 6B. Those elements of the circuit arrangement 620 which correspond to the circuit arrangement 600 shown in FIG. 6A and described above are provided with the same reference symbol. Only those components of the circuit arrangement 620 which deviate from the circuit arrangement 600 shown in FIG. 6A are described in more detail below.

The circuit arrangement 620 has a calibration device 621 that can be coupled to the first circuit unit 602 and serves for calibrating the circuit arrangement 620, which is set up in such a way that a second electrical reference potential can be applied to the first circuit unit 602 by means of the calibration device 621, the first circuit unit 602 being coupled either to the calibration device 621 or to the sensor electrode 601.

What is particularly advantageous about the circuit arrangement 620 shown in FIG. 6B is that the sensor electrode 601 can optionally be decoupled from the first circuit unit 602 and can instead be coupled to the calibration device 621, a reference current source 621a being the essential component thereof. A calibration of the circuit arrangement 620 may be performed by means of a calibration current generated by the calibration device 621. This is advantageous particularly when the exact value of the capacitance C of the first capacitor 604 is not known.

In addition to statistical fluctuations of the capacitance of the first capacitor 604 owing to variations in the process technology during the method for producing the first capacitor 604, the parasitic capacitances of the circuit arrangement 620, which can be calculated only with great complexity or cannot at all be calculated exactly, make a significant contribution to the total capacitance of the storage node and critically influence the resulting output frequency in which the current signal to be registered is coded. Offset voltages, in particular of the second comparator 610 in the current-frequency converter, and possible leakage currents also have a direct influence on the output frequency to be registered. As shown in FIG. 6B, the calibration device 621 has a reference current source 621a that can be connected in, provides a known sensor current, or increases or reduces the latter by a specific magnitude if the reference current source 621a is connected in parallel with the sensor. The change in frequency resulting on account of the connecting-in then serves for calibrating the circuit arrangement 620. Such calibration may be carried out in particular before an analyte is applied to the sensor electrode 601. In this case, the sensor electrode 601 does not supply a signal current originating from sensor events, and the output frequency is determined by the reference current of the reference current source 621a.

The optional connection either of the sensor electrode 601 or of the calibration device 621 to the first circuit unit 602 is realized by means of a further switch 622. The switch 622 may be changed over in such a way that the calibration device 621 is connected to the second circuit unit 602 in the operating state shown in FIG. 6B, whereas the sensor electrode 601 is not connected to the first circuit unit 602 in the operating state shown in FIG. 6B. In a complementary scenario corresponding to a changeover of the further switch 622 shown in FIG. 6B, the sensor electrode 601 is connected to the first circuit unit 602, whereas the calibration device 621 is not connected into the first circuit.

A fourth preferred exemplary embodiment of the circuit arrangement 700 according to the invention is described below with reference to FIG. 7. Those components or blocks from FIG. 7 which have a direct counterpart in FIG. 6B are designated in FIG. 7 by the same reference numerals as in FIG. 6B.

Figure 7:
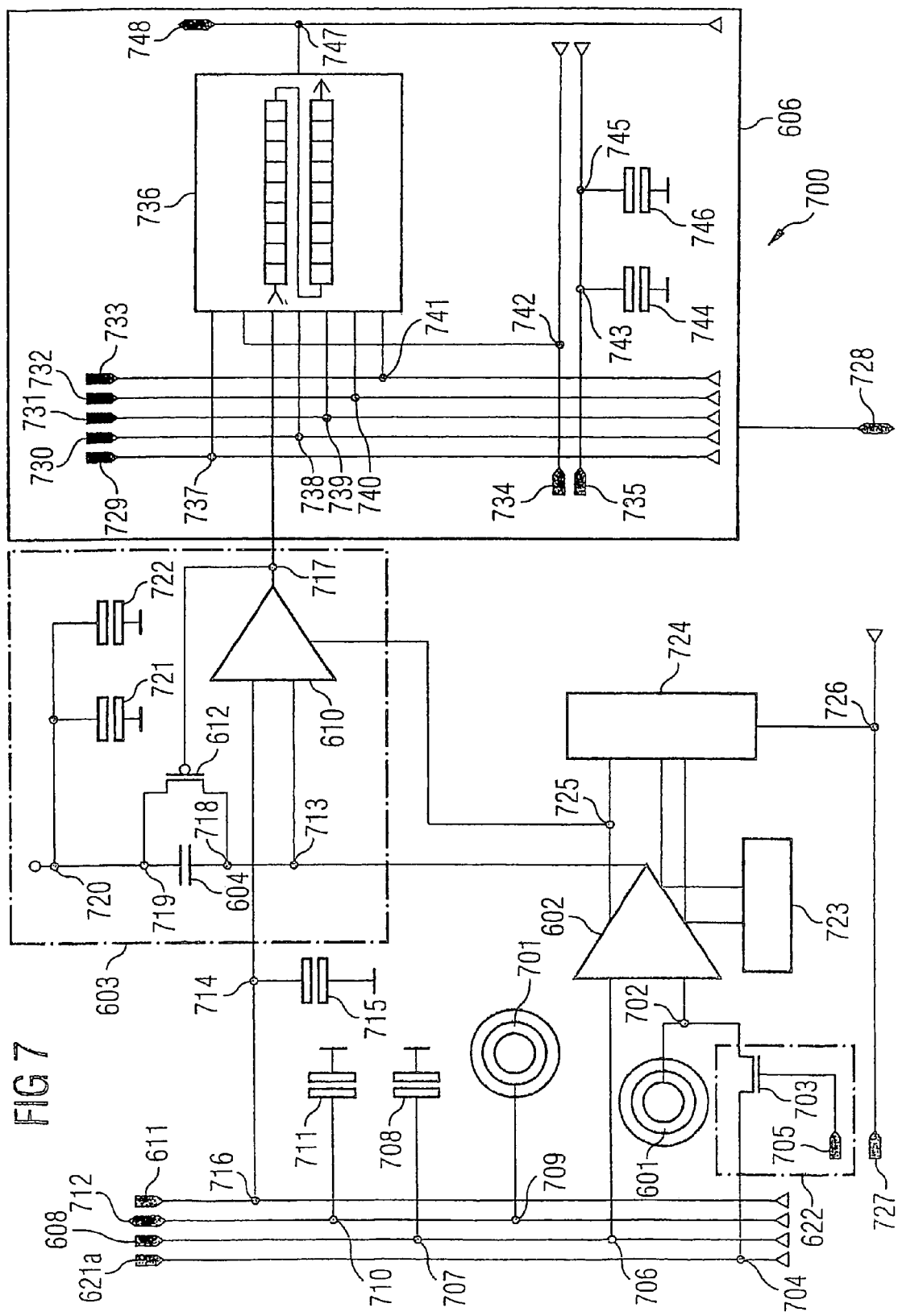
FIG. 7 shows a block diagram of a circuit arrangement in accordance with a fourth exemplary embodiment of the invention.

FIG. 7 illustrates an embodiment of a sensor unit such as may be used in a matrix-type arrangement of a plurality of sensor units.

FIG. 7 shows the sensor electrode 601. Furthermore, FIG. 7 shows a further sensor electrode 701. The sensor electrode 601 is coupled to a first electrical node 702. The first electrical node 702 is coupled to the inverted input of the first circuit unit 602 (functionally a voltage regulator or potentiostat, also referred to as control element 602 hereinafter). Furthermore, the first electrical node 702 is coupled to one source/drain region of a first transistor 703. The other source/drain region of the first transistor 703 is coupled to a second electrical node 704. The second electrical node 704 is coupled to the reference current source 621a of the calibration device. The gate region of the first transistor 703 is coupled to a first voltage supply 705. The first voltage supply 705 and the first transistor 703 form the further switch 622. The noninverted input of the control element 602, which inter alia contains an operational amplifier, is coupled to a third electrical node 706. The third electrical node 706 is identical to a fourth electrical node 707. "Identical" in this sense means "electrically identical", i.e. that the electrical node 706 and the electrical node 707 are (approximately) at the same electrical potential. The fourth electrical node 707 is furthermore coupled to a first capacitance 708 and also to the second voltage source 608. The further electrode 701 is coupled to a fifth electrical node 709. The fifth electrical node 709 is identical to a sixth electrical node 710. The sixth electrical node 710 is coupled to a second capacitance 711. Furthermore, the sixth electrical node 710 is coupled to a second voltage supply 712. The output of the first control element 602 is coupled to a seventh electrical node 713. The seventh electrical node 713 is coupled to the inverted input of the second comparator element 610, which is designed as an operational amplifier. The noninverted input of the second comparator element 610 is coupled to an eighth electrical node 714. The eighth electrical node 714 is coupled to a third capacitance 715. Furthermore, the eighth electrical node 714 is identical to a ninth electrical node 716. The ninth electrical node 716 is coupled to the third voltage source 611. Furthermore, the output of the comparator element 610 is coupled to a tenth electrical node 717. The tenth electrical node 717 is coupled to the gate region of the switch 612, which switch 612 is designed as a transistor. One source/drain region of the switch 612 is coupled to an eleventh electrical node 718. The eleventh electrical node 718 is identical to the seventh electrical node 713—and is coupled to the first capacitor 604. The other source/drain region of the switch 612 is coupled to a twelfth electrical node 719. The twelfth electrical node 719 is on the one hand coupled to the first capacitor 604 and on the other hand identical to a thirteenth electrical node 720. The thirteenth electrical node 720 is coupled to a fourth capacitance 721 and to a fifth capacitance 722. The positive operating voltage is present at the node 720. Furthermore, the circuit arrangement 700 has a first voltage supply unit 723 and a second voltage supply unit 724. A first and a second terminal of the first voltage supply unit 723 are coupled to two further terminals of the control element 602 and these further terminals are furthermore coupled to two terminals of the second voltage supply unit 724. A further terminal of the second voltage supply unit 724 is coupled to a fourteenth electrical node 725. The fourteenth electrical node 725 is coupled both to a further terminal of the control element 602 and to a further terminal of the comparator element 610. A further terminal of the second voltage supply unit 724 is coupled to a fifteenth electrical node 726. The fifteenth electrical node 726 is coupled to a third voltage supply 727.

Furthermore, the counter element 606 is shown in FIG. 7. The counter element 606 is coupled to a fourth voltage supply 728. The counter element 606 has a first control signal 729, a second control signal 730, a third control signal 731, a fourth control signal 732, a fifth control signal 733, a sixth control signal 734 and a seventh control signal 735. Furthermore, the counter element 606 has a counter unit 736. The first control signal 729 is coupled to a sixteenth electrical node 737. The sixteenth electrical node 737 is coupled to an input of the counter unit 736. The second control signal 730 is coupled to a seventeenth electrical node 738. The seventeenth electrical node 738 is coupled to a further input of the counter unit 736. The third control signal 731 is coupled to an eighteenth electrical node 739. The eighteenth electrical node 739 is coupled to a further input of the counter unit 736. The fourth control signal 732 is coupled to a nineteenth electrical node 740. The nineteenth electrical node 740 is coupled to a further input of the counter unit 736. The fifth control signal 733 is coupled to a twentieth electrical node 741. The twentieth electrical node 741 is coupled to a further input of the counter unit 736. The sixth control signal 734 is coupled to a twenty-first electrical node 742. The twenty-first electrical node 742 is coupled to a further input of the counter unit 736. The seventh control signal 735 is coupled to a twenty-second electrical node 743. The twenty-second electrical node 743 is coupled to a sixth capacitance 744. Furthermore, the twenty-second electrical node 743 is identical to a twenty-third electrical node 745. The twenty-third electrical node 745 is coupled to a seventh capacitance 746. A signal in which the counter reading is coded is present at the output of the counter unit 736. This signal is provided to a twenty-fourth electrical node 747. The counter reading signal is communicated serially from the twenty-fourth electrical node 747 to an output terminal 748.

To summarize, essential components of the circuit arrangement 700 shown in FIG. 7 are the two sensor electrodes 601, 701, the first circuit unit 602, the first capacitor 604—serving as storage capacitance—with the switch 612 connected in parallel therewith, said switch being designed as a transistor and serving for resetting the capacitor voltage. This resetting is initiated by means of the second comparator element 610, which is likewise designed as an operational amplifier and which compares the voltage across the first capacitor 604 with the voltage signal of the third voltage source 611 and correspondingly drives the switch 612 designed as a transistor.

It must be emphasized that an independent circuit block for generating a pulse having a constant length is not provided in the realization shown in FIG. 7. A suitable temporal pulse duration results, on account of the circuit shown, automatically from the reaction time of the system "second comparator element 610—first capacitor 604—switch 612" and has values that are sufficiently constant over a large measurement range.

The pulses of the second comparator element 610 are counted in the counter unit 736 of the counter element 606. By means of the control signals, the counter unit 736 can be changed over to a shift register operation, as a result of which the present counter reading is output serially at the output terminal 748.

The circuitry configuration of the first comparator element 607 in the circuit arrangement 700 shown in FIG. 7 is described in more detail below with reference to FIG. 8. Those components shown in FIG. 8 which have a counterpart in FIG. 7 or FIG. 6B, respectively, are provided with the same reference numerals.

FIG. 8 shows the first control element 602 (also referred to as first circuit unit 602). The first electrical node 702 from FIG. 7 is coupled to a first electrical node 801 and the first electrical node 801 is coupled to the noninverted input of the operational amplifier 607 (of the first comparator element 607). The third electrical node 706 from FIG. 7 is coupled to the inverted input 803 of the operational amplifier 607. Furthermore, the operational amplifier 607 is coupled to a first terminal 804a, a second terminal 804b and a third terminal 804c. The first terminal 804a is coupled to the second voltage supply unit 724. The second terminal 804b and the third terminal 804b are respectively coupled to the first voltage supply unit 823. An output 805 of the operational amplifier 607 is coupled to a second electrical node 806. The second electrical node 806 is coupled to a capacitor 807. The capacitor 807 is coupled to a third electrical node 808. The third electrical node 808 is identical to the first electrical node 801. Furthermore, the second electrical node 806 is coupled to the gate region of the transistor 609. One source/drain region of the transistor 609 is coupled to the third electrical node 808 and the other source/drain region of the transistor 609 is coupled to an output terminal 810, which output terminal 810 corresponds to the output of the first control element 602 in FIG. 7.

The circuitry construction of the operational amplifier 607 from FIG. 8 is described in more detail below with reference to FIG. 9. The inputs and outputs or the terminals of the operational amplifier 607 that are shown in FIG. 8 are provided with the same reference numerals in FIG. 9.

Figure 9:
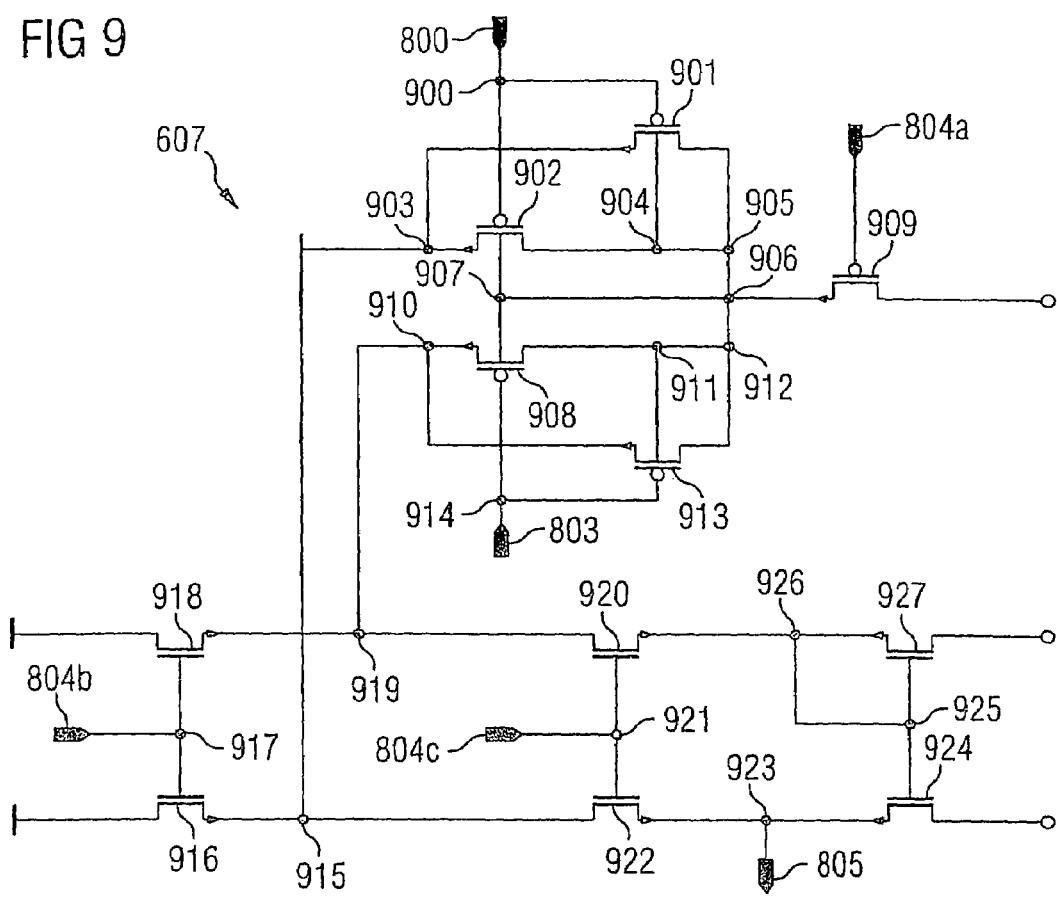
FIG. 9 shows a further block diagram showing the construction of the first comparator element shown in FIG. 8.

The noninverted input 800 of the operational amplifier 607 as shown in FIG. 9 is coupled to a first electrical node 900. The first electrical node 900 is coupled to the gate region of a first transistor 901. Furthermore, the first electrical node 900 is coupled to the gate region of a second transistor 902. One source/drain region of the first transistor 901 is coupled to a second electrical node 903. The other source/drain region of the second transistor 902 is coupled to a third electrical node 904. The third electrical node 904 is coupled to the first transistor 901 and is identical to a fourth electrical node 905. The fourth electrical node 905 is coupled to the other source/drain region of the first transistor 901. Furthermore, the fourth electrical node 905 is identical to a fifth electrical node 906. The fifth electrical node 906 is identical to a sixth electrical node 907. The sixth electrical node 907 is coupled both to the second transistor 902 and to a third transistor 908. The fifth electrical node 906 is furthermore coupled to one source/drain region of a fourth transistor 909. The gate region of the fourth transistor 909 is coupled to the first terminal 804a of the operational amplifier 607. One source/drain region of the third transistor 908 is coupled to a seventh electrical node 910. The other source/drain region of the third transistor 908 is coupled to an eighth electrical node 911. The eighth electrical node 911 is identical to a ninth electrical node 912. The ninth electrical node 912 is coupled to one source/drain region of a fifth transistor 913. Furthermore, the ninth electrical node 912 is identical to the fifth electrical node 906. The other source/drain region of the fifth transistor 913 is coupled to the seventh electrical node 910. Furthermore, the eighth electrical node 911 is coupled to the fifth transistor 913. The gate region of the third transistor 908 is coupled to a tenth electrical node 914. The tenth electrical node 914 is furthermore coupled to the gate region of the fifth transistor 913. Furthermore, the tenth electrical node 914 is coupled to the inverted input 803 of the operational amplifier 607. The second electrical node 903 is identical to an eleventh electrical node 915. The eleventh electrical node 915 is coupled to one source/drain region of a sixth transistor 916. The gate region of the sixth transistor 916 is coupled to a twelfth electrical node 917. The twelfth electrical node 917 is coupled to the second terminal 804b of the comparator unit 607. Furthermore, the twelfth electrical node 917 is coupled to the gate region of a seventh transistor 918. One source/drain region of the seventh transistor 918 is coupled to a thirteenth electrical node 919. The thirteenth electrical node 919 is identical to the seventh electrical node 910. Furthermore, the thirteenth electrical node 919 is coupled to the first source/drain region of an eighth transistor 920. The gate region of the eighth transistor 920 is coupled to a fourteenth electrical node 921. The fourteenth electrical node 921 is coupled to the third terminal 804c of the operational amplifier 607 and is furthermore coupled to the gate region of a ninth transistor 922. One source/drain region of the ninth transistor 922 is coupled to the eleventh electrical node 915 and the other source/drain region of the ninth transistor 922 is coupled to a fifteenth electrical node 923. The fifteenth electrical node 923 is coupled to the output 805 of the operational amplifier 607 and is furthermore coupled to one source/drain region of a tenth transistor 924. The gate region of the tenth transistor 924 is coupled to a sixteenth electrical node 925. The sixteenth electrical node 925 is furthermore identical to a seventeenth electrical node 926. The seventeenth electrical node 926 is coupled to one source/drain region of an eleventh transistor 927, and the gate region of the eleventh transistor 927 is coupled to the sixteenth electrical node 925. Furthermore, the seventeenth electrical node 926 is coupled to the other source/drain region of the eighth transistor 920.

A preferred exemplary embodiment of the second comparator element 610 shown in FIG. 6B, FIG. 7 is described below with reference to FIG. 10.

Figure 10:
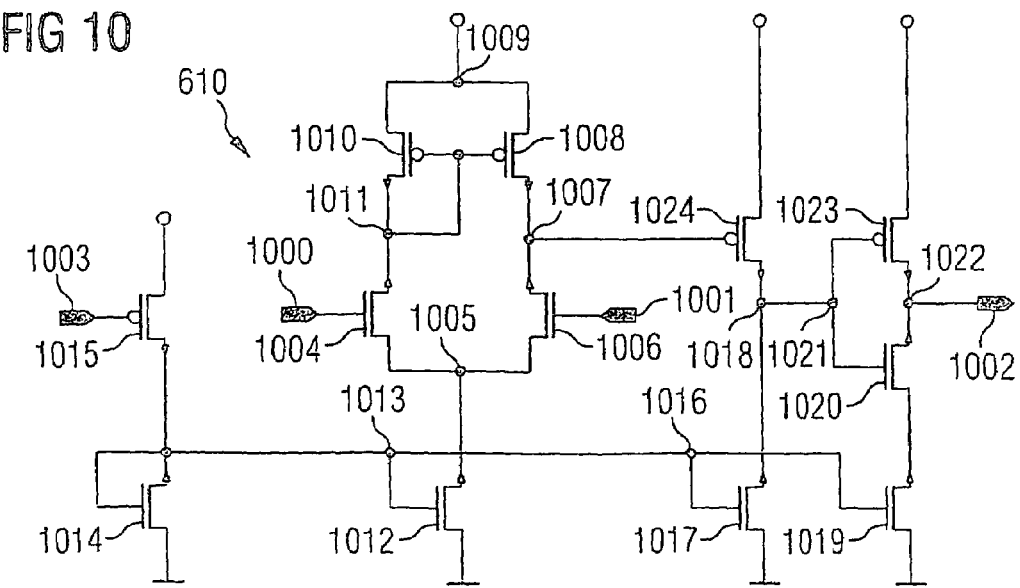
FIG. 10 shows a further block diagram showing the construction of a second comparator element shown in FIG. 7.

The comparator element 610 shown in FIG. 10 has a first input 1000 coupled to the seventh electrical node 713 shown in FIG. 7. The comparator element 610 furthermore has a second input 1001 coupled to the eighth electrical node 714 from FIG. 7. Furthermore, the comparator element 610 has an output 1002 coupled to the tenth electrical node 717 of the circuit arrangement 700 from FIG. 7. Furthermore, the second comparator element 610 has a supply input 1003, which is coupled to the fourteenth electrical node 725 of the circuit arrangement 700 and which is thus indirectly electrically coupled to the second voltage supply unit 724.

The first input 1000 is coupled to the gate region of a first transistor 1004. One source/drain region of the first transistor 1004 is coupled to a first electrical node 1005. The first electrical node 1005 is furthermore coupled to one source/drain region of a second transistor 1006. The gate region of the second transistor 1006 is coupled to the second input 1001 of the second comparator element 610. The other source/drain region of the second transistor 1006 is coupled to a second electrical node 1007. The second electrical node 1007 is coupled to one source/drain region of a third transistor 1008. The other source/drain region of the third transistor 1008 is coupled to a third electrical node 1009. The third electrical node 1009 is coupled to one source/drain region of a fourth transistor 1010. The gate region of the third transistor 1008 is coupled to the gate region of the fourth transistor 1010, and the gate region of the fourth transistor 1010 is furthermore coupled to a fourth electrical node 1011. The fourth electrical node 1011 is coupled to the other source/drain region of the first transistor 1004. Furthermore, the first electrical node 1005 is coupled to one source/drain region of a fifth transistor 1012. The gate region of the fifth transistor 1012 is coupled to a fifth electrical node 1013. The fifth electrical node 1013 is coupled to the gate region and to one source/drain region of a sixth transistor 1014. One source/drain region of the sixth transistor 1014 is coupled to one source/drain region of a seventh transistor 1015.

Furthermore, the gate region of the seventh transistor 1015 is coupled to the supply input 1003. The fifth electrical node 1013 is identical to a sixth electrical node 1016. Furthermore, the sixth electrical node 1016 is coupled to the gate region of an eighth transistor 1017. One source/drain region of the eighth transistor 1017 is coupled to a seventh electrical node 1018. The sixth electrical node 1016 is furthermore coupled to the gate region of a ninth transistor 1019. One source/drain region of the ninth transistor 1019 is coupled to one source/drain region of a tenth transistor 1020. The seventh electrical node 1018 is identical to an eighth electrical node 1021. The gate region of the tenth transistor 1020 is coupled to the eighth electrical node 1021. The other source/drain region of the tenth transistor 1020 is coupled to a ninth electrical node 1022. The ninth electrical node 1022 is coupled to the output 1002 of the second comparator element 610. Furthermore, the ninth electrical node 1022 is coupled to one source/drain region of an eleventh transistor 1023. The eighth electrical node 1021 is coupled to the gate region of the eleventh transistor 1023. Furthermore, the seventh electrical node 1018 is coupled to one source/drain region of a twelfth transistor 1024. The gate region of the twelfth transistor 1024 is coupled to the second electrical node 1007.

A preferred exemplary embodiment of a counter element of the circuit arrangement according to the invention is described below with reference to FIG. 11.

Figure 11:
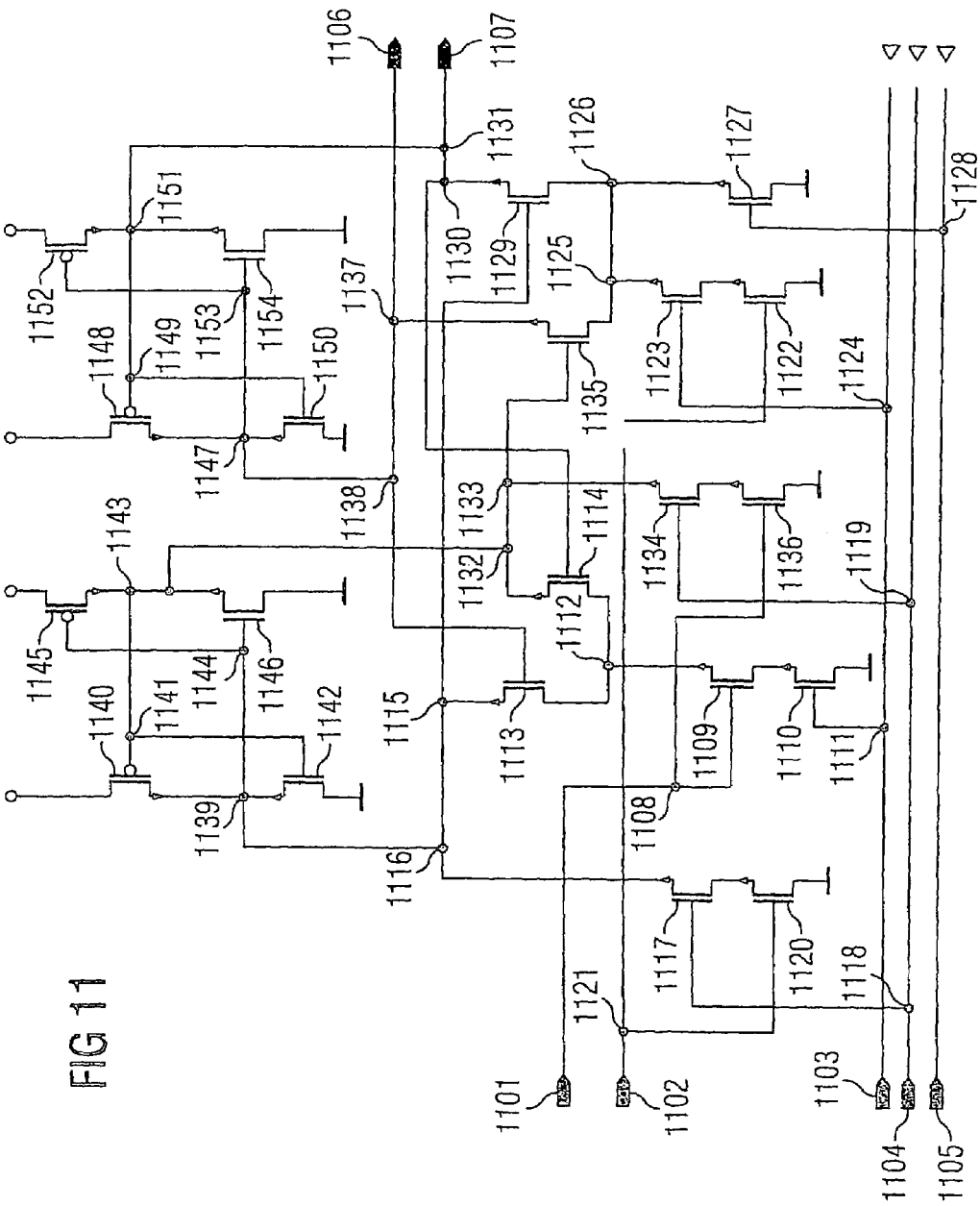
FIG. 11 shows a further block diagram showing the construction of a stage of the counter and of the shift register, respectively, from FIG. 7.

The counter element 1100 shown in FIG. 11 has a first input 1101, a second input 1102, a third input 1103, a fourth input 1104 and a fifth input 1105. Furthermore, the counter element 1100 has a first output 1106 and a second output 1107. The first input 1101 is coupled to a first electrical node 1108. The first electrical node 1108 is coupled to the gate region of a first transistor 1109. One source/drain region of the first transistor 1109 is coupled to one source/drain region of a second transistor 1110. The gate region of the second transistor 1110 is coupled to a second electrical node 1111. The second electrical node 1111 is coupled to the third input 1103 of the counter element 1100. The other source/drain region of the first transistor 1109 is coupled to a third electrical node 1112. The third electrical node 1112 is coupled to one source/drain region of a third transistor 1113. Furthermore, the third electrical node 1112 is coupled to one source/drain region of a fourth transistor 1114. The other source/drain region of the third transistor 1113 is coupled to a fourth electrical node 1115. The fourth electrical node 1115 is coupled to a fifth electrical node 1116. The fifth electrical node 1116 is coupled to one source/drain region of a fifth transistor 1117. The gate region of the fifth transistor 1117 is coupled to a sixth electrical node 1118. The sixth electrical node 1118 is coupled to the fourth input 1104 of the counter element 1100. Furthermore the sixth electrical node 1118 is identical to a seventh electrical node 1119. The other source/ drain region of the fifth transistor 1117 is coupled to one source/drain region of a sixth transistor 1120. The gate region of the sixth transistor 1120 is coupled to an eighth electrical node 1121. The eighth electrical node 1121 is coupled to the second input 1102 of the counter element 1100. Furthermore, the eighth electrical node 1121 is coupled to the gate region of a seventh transistor 1122. One source/drain region of the seventh transistor 1122 is coupled to one source/drain region of an eighth transistor 1123. The gate region of the eighth transistor 1123 is coupled to a ninth electrical node 1124. The ninth electrical node 1124 is identical to the second electrical node 1111. The other source/drain region of the eighth transistor 1123 is coupled to a tenth electrical node 1125. The tenth electrical node 1125 is identical to an eleventh electrical node 1126. The eleventh electrical node 1126 is coupled to one source/drain region of a ninth transistor 1127. The gate region of the ninth transistor 1127 is coupled to a twelfth electrical node 1128. The twelfth electrical node 1128 is coupled to the fifth input 1105 of the counter element 1100. The eleventh electrical node 1126 is coupled to one source/drain region of a tenth transistor 1129. The gate region of the tenth transistor 1129 is coupled to the fourth electrical node 1115. The other source/drain region of the tenth transistor 1129 is coupled to a thirteenth electrical node 1130. The thirteenth electrical node 1130 is identical to a fourteenth electrical node 1131. The fourteenth electrical node 1131 is coupled to the second output 1107 of the counter element 1100. Furthermore, the thirteenth electrical node 1130 is coupled to the gate region of the fourth transistor 1114. The other source/drain region of the fourth transistor 1114 is coupled to a fifteenth electrical node 1132. The fifteenth electrical node 1132 is identical to a sixteenth electrical node 1133. The sixteenth electrical node 1133 is coupled to one source/drain region of an eleventh transistor 1134. The sixteenth electrical node 1133 is furthermore coupled to the gate region of a twelfth transistor 1135. One source/drain region of the twelfth transistor 1135 is coupled to the tenth electrical node 1125. The gate region of the eleventh transistor 1134 is coupled to the seventh electrical node 1119. The other source/drain region of the eleventh transistor 1134 is coupled to one source/drain region of a thirteenth transistor 1136. The gate region of the thirteenth transistor 1136 is coupled to the first electrical node 1108. The other source/drain region of the twelfth transistor 1135 is coupled to a seventeenth electrical node 1137. The seventeenth electrical node 1137 is identical to an eighteenth electrical node 1138. Furthermore, the seventeenth electrical node 1137 is coupled to the first output 1106 of the counter element 1100. The gate region of the third transistor 1113 is furthermore coupled to the eighteenth electrical node 1138. The fifth electrical node 1116 is identical to a nineteenth electrical node 1139. The nineteenth electrical node 1139 is coupled to one source/drain region of a fourteenth transistor 1140. The gate region of the fourteenth transistor 1140 is coupled to a twentieth electrical node 1141. The twentieth electrical node 1140 is coupled to the gate region of a fifteenth transistor 1142. The nineteenth electrical node 1139 is coupled to one source/drain region of the fifteenth transistor 1142. The gate region of the fourteenth transistor 1140 is coupled to a twenty-first electrical node 1143. A twenty-second electrical node 1144 is identical to the nineteenth electrical node 1139. The twenty-second electrical node 1143 is coupled to one source/drain region of a sixteenth transistor 1145. The gate region of the sixteenth transistor 1145 is coupled to the twenty-second electrical node 1144. The gate region of a seventeenth transistor 1146 is coupled to the twenty-second electrical node 1144. One source/drain region of the seventeenth transistor 1146 is coupled to the twenty-first electrical node 1143. The twenty-second electrical node 1143 is identical to the fifteenth electrical node 1132. Furthermore, the twenty-second electrical node 1144 is coupled to the gate region of a seventeenth transistor 1146, one source/drain region of the seventeenth transistor 1146 being coupled to the twenty-first electrical node 1143. The nineteenth electrical node 1138 is identical to a twenty-third electrical node 1147. The twenty-third electrical node 1147 is coupled to one source/drain region of an eighteenth transistor 1148. The gate region of the eighteenth transistor 1148 is coupled to a twenty-fourth electrical node 1149. The twenty-fourth electrical node 1149 is coupled to the gate region of a nineteenth transistor 1150. The twenty-third electrical node 1147 is coupled to one source/drain region of the nineteenth transistor 1150. The gate region of the eighteenth transistor 1148 is coupled to a twenty-fifth electrical node 1151. The twenty-fifth electrical node 1151 is coupled to one source/drain region of a twentieth transistor 1152. The gate region of the twentieth transistor 1152 is coupled to a twenty-sixth electrical node 1153. The twenty-sixth electrical node 1153 is identical to the twenty-third electrical node 1147. The twenty-fifth electrical node 1151 is coupled to one source/drain region of a twenty-first transistor 1154. The gate region of the twenty-first transistor 1154 is coupled to the twenty-sixth electrical node 1153. The twenty-fifth electrical node 1151 is identical to the fourteenth electrical node 1131. The first electrical node 1108 is coupled to the gate region of the thirteenth transistor 1136.

FIG. 12 shows a preferred exemplary embodiment of the sensor arrangement 1200 according to the invention having a plurality of circuit arrangements 1201 (each of which may be configured like the circuit arrangement 700 shown in FIG. 7) arranged in matrix form on a chip 1202. Each of the circuit arrangements 1200 may be operated as a sensor independently of the other circuit arrangements. If the circuit arrangements 1200 are configured as sensors for detecting different molecules (e.g. each has capture molecules that can be hybridized with a specific type of DNA strands), then a parallel analysis of a liquid to be investigated is possible by means of the sensor arrangement 1200. In this case, circuit units that serve for driving, for voltage and current supply and for read-out of the sensor cells are situated at the edge of the matrix-type arrangement of sensor electrodes.

These circuit units supply for example the reference current 621a for calibrating the individual sensor arrays, supply and reference voltages for the control unit 602 and comparator unit 603 contained in the sensor elements, and also the digital control signals for the counter 736. These are, in particular, a reset signal for the counter, a changeover signal for the counter/shift register operation, and also, if appropriate, a changeover signal for further capacitors connected in parallel with the first capacitor 604. In particular, the units at the edge of the matrix contain the circuits for preevaluation of the measured signals, in particular for read-out, storage and further processing of the counter contents of the individual sensor elements.

The advantages of the sensor circuit according to the invention are particularly manifested in an arrangement of a multiplicity of sensor units on a semiconductor chip since each sensor element is able autonomously to measure the current signal of the sensor electrodes and to store it in the form of a digital counter signal within the sensor element. At the same time, the electrode potential is held constant at the desired potential. Said counter signal can then be interrogated and processed further at an arbitrary point in time by means of the circuit units at the edge of the matrix.

On account of the high word width of the binary counter 736, it is expedient to serially read out the counter reading from the sensor elements since, in the case of a parallel read-out, very wide data buses would have to be routed over the entire matrix. The serial outputting of the counter reading is effected by changing over the binary counter 736 from the counter operating mode to the shift register operating mode. By the application of a clock signal, the counter content, that is to say the individual data bits in the counter stages, is then progressively advanced into the respectively downstream counter stage, so that all the data bits of an n-stage counter are output at the output of the counter after n clock pulses. The number of required counter stages is associated directly with the required dynamic range. By way of example, if the intention is to register a measurement signal with an accuracy of 6 bits in a measurement range of 5 decades, a counter having a word width of 23 bits is necessary. The use of serial protocols for data communication is advantageous in particular also because this simultaneously simplifies communication with the read-out device into which the chip is inserted.

The use of a counter circuit within the sensor unit is not absolutely necessary; instead of this, it is also possible, by way of example, to directly output the output signal of the pulse transmitter 613 in which the measured current intensity at the sensor electrodes is coded in the form of a frequency. The circuit units at the edge of the matrix then serve for measuring and further processing the frequencies or pulse durations of the individual sensor units.

The invention claimed is:

1. A circuit arrangement, comprising:
   a sensor electrode;
   a first circuit unit, which is electrically coupled to the sensor electrode; and
   a second circuit unit, which has a first capacitor,
   wherein the first circuit unit holds an electrical potential of the sensor electrode in a predetermined first reference range around a predetermined electrical desired potential by coupling the first capacitor and the sensor electrode such that there is a matching of their electrical potentials, and
   wherein if the second circuit unit detects the electrical potential of the first capacitor being outside a second reference range, the second circuit unit brings the first capacitor to a first electrical reference potential.

2. The circuit arrangement as claimed in claim 1, further comprising a counter element, which is electrically coupled to the second circuit unit, and counts a number and/or a temporal sequence of the events.

3. The circuit arrangement as claimed in claim 2, wherein the counter element registers the temporal sequence of the events in at least two time intervals at a temporal distance from one another.

4. The circuit arrangement as claimed in claim 1, further comprising a calibration device coupled to the first circuit unit and calibrating the circuit arrangement,
   wherein a second electrical reference potential is applied to the first circuit unit by the calibration device, and the first circuit unit is coupled either to the calibration device or to the sensor electrode.

5. The circuit arrangement as claimed in claim 1, wherein the first circuit unit has a first comparator element having two inputs and an output,
   the first input being coupled to the sensor electrode such that the first input is at the electrical potential of the sensor electrode,
   the second input being at a third electrical reference potential, which defines the electrical desired potential, and
   the first comparator element generating an electrical signal at its output such that the electrical potential of the sensor electrode is held in the predetermined first reference range around the predetermined electrical desired potential.

6. The circuit arrangement as claimed in claim 1, wherein the first circuit unit has a variable nonreactive resistor, which couples the sensor electrode to the first capacitor of the second circuit unit such that the potential of the sensor electrode is held in the predetermined first reference range around the predetermined electrical desired potential.

7. The circuit arrangement as claimed in claim 5, wherein the first circuit unit comprises a transistor having a gate region coupled to the output of the first comparator element, a first source/drain region coupled to the sensor electrode, and a second source/drain region coupled to the first capacitor.

8. The circuit arrangement as claimed in claim 5, wherein the second circuit unit has a second comparator element having two inputs and an output,
   the first input being coupled to the first capacitor such that the first input is at the electrical potential of the first capacitor,
   the second input being at a fourth electrical reference potential, which defines the second electrical reference range, and
   the second comparator element generating an electrical signal at its output such that, if the electrical potential of the first capacitor exceeds the fourth electrical reference potential, the first capacitor is brought to the first electrical reference potential.

9. The circuit arrangement as claimed in claim 5, wherein the second circuit unit has a second comparator element having two inputs and an output,
   the first input being coupled to the first capacitor such that the first input is at the electrical potential of the first capacitor,
   the second input being at a fourth electrical reference potential, which defines the second electrical reference range, and
   the second comparator element generating an electrical signal at its output such that, if the electrical potential of the first capacitor falls below the fourth electrical reference potential, the first capacitor is brought to the first electrical reference potential.

10. The circuit arrangement as claimed in claim 8, wherein the first and/or the second comparator element is an operational amplifier.

11. The circuit arrangement as claimed in claim 9, wherein the first and/or the second comparator element is an operational amplifier.

12. The circuit arrangement as claimed in claim 1, wherein the second circuit unit has at least one second capacitor, the circuit arrangement being set up such that either one of the at least one second capacitor or the first capacitor or at least two of the capacitors is/are simultaneously connected into the circuit arrangement.

13. The circuit arrangement as claimed in claim 1, which is designed as an integrated circuit.

14. An electrochemical sensor comprising a circuit arrangement as claimed in claim 1.

15. A sensor arrangement comprising a plurality of circuit arrangements as claimed in claim 1.

16. The sensor arrangement as claimed in claim 15, wherein each of the circuit arrangements is set up as an autonomously operating sensor element.

17. The sensor arrangement as claimed in claim 15, wherein the circuit arrangements are essentially arranged in matrix form.

18. The sensor arrangement as claimed in claim 15, comprising:
   a central drive circuit;
   a central supply circuit; and/or
   a central read-out circuit,
      wherein the circuit/circuits is/are coupled to at least one portion of the circuit arrangements.

19. A method for processing a current signal provided via a sensor electrode, in a circuit arrangement having the sensor electrode, a first circuit unit, which is electrically coupled to the sensor electrode, and a second circuit unit, which has a first capacitor, the method comprising the steps of:
   holding the electrical potential of the sensor electrode in a predetermined first reference range around a predetermined electrical desired potential by coupling the first capacitor and the sensor electrode such that there is a matching of their electrical potentials;
   if the electrical potential of the first capacitor is outside the second reference range, the second circuit unit performing the steps of:
   detecting this event; and
   bringing the first capacitor to the first electrical reference potential.

20. The method as claimed in claim 19, wherein the temporal sequence of the events is counted by means of a counter element electrically coupled to the second circuit unit.

21. The method as claimed in claim 20, wherein the counter element is used to register the temporal sequence of the events in at least two time intervals at a temporal distance from one another.

* * * * *